(12) United States Patent
Taddei et al.

(10) Patent No.: US 9,346,745 B2
(45) Date of Patent: May 24, 2016

(54) PROCESS FOR PRODUCING ALISKIREN

(75) Inventors: Maurizio Taddei, Monteriggioni (IT); Adele Russo, Baronissi (IT); Elena Cini, Gambassi Terme (IT); Renata Riva, Genoa (IT); Marcello Rasparini, Cura Carpignano (IT); Luca Carcone, Cervaro (IT); Luca Banfi, Genoa (IT); Romina Vitale, Ovada (IT); Stephen Roseblade, Cambridge (GB); Antonio Carlo Zanotti-Gerosa, Cambridge (GB)

(73) Assignee: CHEMO IBERICA, S.A., Barcelona (ES)

(*) Notice: Subject to any disclaimer, the term of this patent is extended or adjusted under 35 U.S.C. 154(b) by 471 days.

(21) Appl. No.: 13/701,440

(22) PCT Filed: Jun. 3, 2011

(86) PCT No.: PCT/EP2011/059196
§ 371 (c)(1),
(2), (4) Date: Nov. 30, 2012

(87) PCT Pub. No.: WO2011/151442
PCT Pub. Date: Dec. 8, 2011

(65) Prior Publication Data
US 2013/0071899 A1    Mar. 21, 2013

(30) Foreign Application Priority Data

Jun. 4, 2010 (IT) .............................. MI2010A1008
Dec. 10, 2010 (IT) .............................. MI2010A2271

(51) Int. Cl.

| | | |
|---|---|---|
| C07C 237/22 | (2006.01) |
| C07C 231/14 | (2006.01) |
| C07C 67/00 | (2006.01) |
| C07C 67/30 | (2006.01) |
| C07C 67/303 | (2006.01) |
| C07C 67/343 | (2006.01) |
| C07C 231/18 | (2006.01) |
| C07C 269/02 | (2006.01) |
| C07D 263/24 | (2006.01) |
| C07D 307/33 | (2006.01) |
| C12P 7/40 | (2006.01) |
| C12P 13/02 | (2006.01) |
| C12P 41/00 | (2006.01) |
| C07D 263/22 | (2006.01) |
| C12P 7/00 | (2006.01) |
| C12P 7/24 | (2006.01) |

(52) U.S. Cl.
CPC .............. *C07C 231/14* (2013.01); *C07C 67/00* (2013.01); *C07C 67/30* (2013.01); *C07C 67/303* (2013.01); *C07C 67/343* (2013.01); *C07C 231/18* (2013.01); *C07C 269/02* (2013.01); *C07D 263/22* (2013.01); *C07D 263/24* (2013.01); *C07D 307/33* (2013.01); *C12P 7/00* (2013.01); *C12P 7/24* (2013.01); *C12P 7/40* (2013.01); *C12P 13/02* (2013.01); *C12P 41/002* (2013.01); *C12P 41/005* (2013.01); *C12Y 101/01* (2013.01); *C12Y 301/01001* (2013.01); *C07B 2200/07* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,559,111 | A | 9/1996 | Goschke et al. |
| 2008/0306311 | A1 | 12/2008 | Daeuwel et al. |

FOREIGN PATENT DOCUMENTS

| | | |
|---|---|---|
| EP | 1303478 | 5/2004 |
| WO | 02/02500 | 1/2002 |
| WO | 02/08172 | 1/2002 |
| WO | 2006/083924 | 8/2006 |
| WO | 2009/007461 | 1/2009 |
| WO | 2009/080773 | 7/2009 |
| WO | 2010/010165 | 1/2010 |

OTHER PUBLICATIONS

Boogers, J.A.F. et al., "A Mixed=Ligand Approach Enables the Asymmetric Hydrogenation of an a-Isopropylcinnamic Acid en Route to the Renin Inhibitor Aliskiren", Organic Process Research and Development, vol. 11, pp. 585-591, 2007.
Dong, H. et al., "Practical synthesis of an orally active renin inhibitor aliskiren", Tetrahedron Letters, vol. 46, pp. 6337-6340, 2005.

(Continued)

*Primary Examiner* — Yong Chu
*Assistant Examiner* — Ana Z Muresan
(74) *Attorney, Agent, or Firm* — Fish & Tsang, LLP

(57) ABSTRACT

A new route of synthesis of the compound Aliskiren of formula (I), used in the treatment of hypertension, is described.

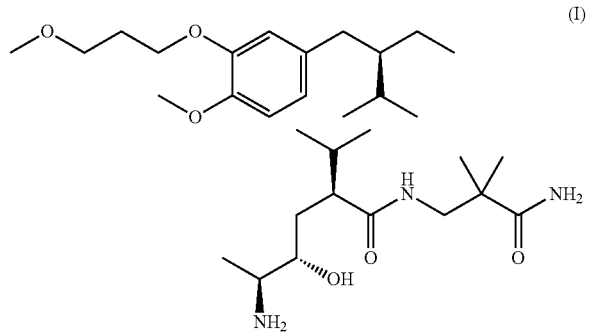

(I)

16 Claims, No Drawings

(56) References Cited

OTHER PUBLICATIONS

Jiang, B. et al., "Stereoselective synthesis of Certonardolsterol D3", Tetrahedron, vol. 64, pp. 9738-9744, 2008.

Rueger, H. et al., "A convergent synthesis approach towards CGP60536B, a non-peptide orally potent renin inhibitor, via an enantiomerically pure ketolactone intermediate", Tetrahedron Letters, vol. 41, pp. 10085-10089, 2000.

Yuan, Z. et al, "Graphical Synthetic Routes of Aliskiren", Chinese Journal of Pharaceuticals, 2009, vol. 40, No. 6., pp. 468-473.

PROCESS FOR PRODUCING ALISKIREN

FIELD OF THE INVENTION

The present invention relates to a process for producing Aliskiren.

PRIOR ART

Aliskiren is the compound having the IUPAC name (2S,4S,5S,7S)—N-(2-carbamoyl-2-methylpropyl)-5-amino-4-hydroxy-2,7-diisopropyl-8-[4-methoxy-3-(3-methoxypropoxy)phenyl]-octanamide and the following structure (I):

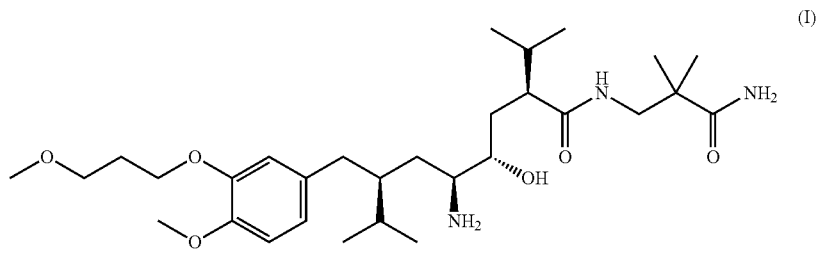 [SMILES: COCCCOc1cc(C[C@@H](C[C@H](N)[C@@H](O)C[C@H](C(=O)NCC(C)(C)C(N)=O)C(C)C)C(C)C)ccc1OC]

This compound is the first molecule known to be capable of directly inhibiting the functionality of renin, an enzyme involved in the processes of regulation of blood pressure, and is used in the treatment of hypertension.

Aliskiren is generally marketed in the form of hemifumarate, with the name Rasilez® in Europe and Tekturna® in the USA, and can be administered in combination with other known antihypertensives, such as hydrochlorothiazide (HCTZ).

The production of compounds of the class of amides of δ-amino-γ-hydroxy-ω-arylalkanoic acids, of which Aliskiren is a member, as well as of related compounds (such as hemifumarate), is described in U.S. Pat. No. 5,559,111.

Patent EP 1,303,478 B1 teaches a route of synthesis of Aliskiren currently used for its industrial production. However, there are some problems in the synthesis described in this document: firstly it requires the use of Grignard reagents, which are known to be difficult to use on an industrial scale, owing to the highly exothermic nature of the reactions in which they take part; secondly, this synthesis requires the use of aluminium diethyl chloride, a pyrophoric and corrosive reagent, requiring the use of specialized equipment.

The aim of the present invention is to provide a novel process for producing Aliskiren that allows the disadvantages of the prior art to be overcome, as well as to provide a novel compound that can be used in the process.

SUMMARY OF THE INVENTION

These aims are achieved according to the present invention, which in a first aspect relates to a process comprising the following operations:

A) preparing a beta-dicarbonyl intermediate of formula (V):

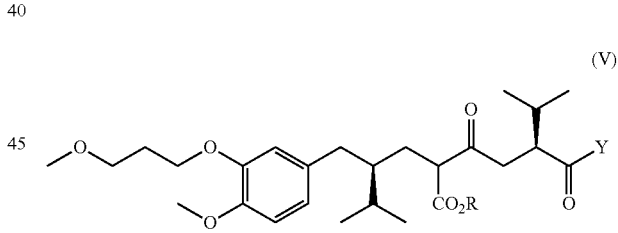

in which R is selected from hydrogen, alkyl or substituted alkyl, aryl or substituted aryl; and Y is selected from: a group —$OR^1$, in which $R^1$ has the same meanings defined above for R; the radical (S)-4-benzyloxazolidin-2-on-3-yl; or the radical 2-carbamoyl-2-methylpropylamine, of formula:

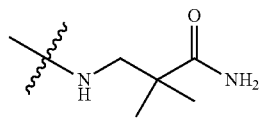 [SMILES: *NCC(C)(C)C(N)=O]

B) transforming compound (V) into the intermediate of formula (VII):

C.i.3): intramolecular reaction between the alcoholic group and the isocyanate group of compound (VII″) to give the cyclic carbamate (VIII):

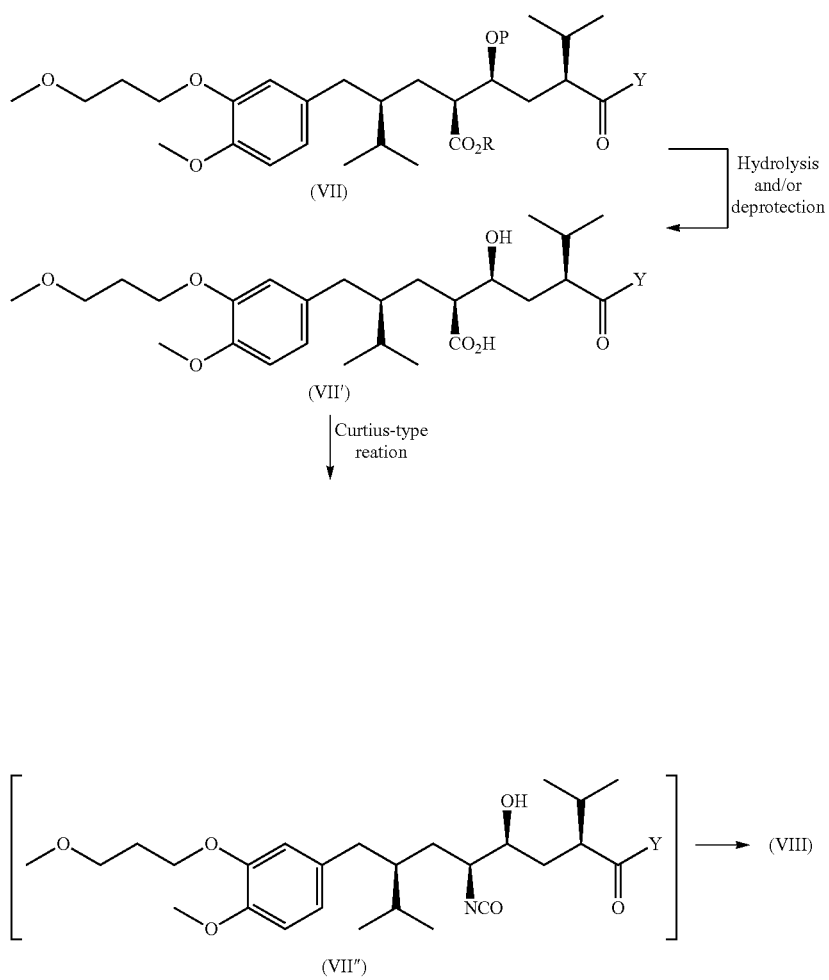

in which P is selected from the radicals hydrogen (H); acyl, $R^2C(O)—$, in which $R^2$ has the same meanings defined above for R, in particular acetyl, $CH_3C(O)—$; silyl, $R^3_3Si—$, in which $R^3$ has the same meanings defined above for R, in particular trimethylsilyl, $(CH_3)_3Si—$, tert-butyldimethylsilyl, $(t\text{-}Bu)Me_2Si—$ and tert-butyl-diphenylsilyl $(t\text{-}Bu)Ph_2Si$; and carbamoyl, $R^4_2NC(O)—$, in which $R^4$ has the same meanings defined above for R, in particular dimethylcarbamoyl;

C) transforming intermediate (VII) into a cyclic carbamate or an amino-lactone, of formula (VIII) or (IX") respectively, in which W is hydrogen or $—C(O)OR^5$ and in which $R^5$ has the same meanings defined above for R:

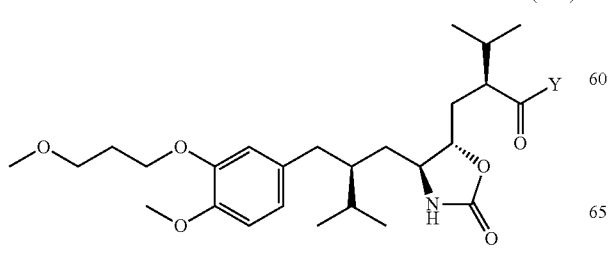

-continued

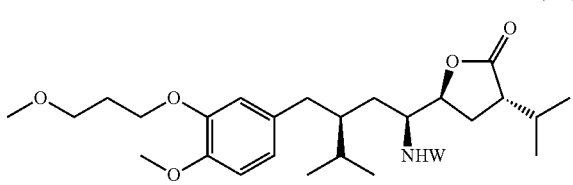

D) transforming the cyclic carbamate (VIII) or the aminolactone (IX") into Aliskiren of formula (I).

Compound (V) can be prepared (operation A of the process of the invention) according to two alternative routes of synthesis A.i) and A.ii).

DETAILED DESCRIPTION OF THE INVENTION

The reaction pathway A.i) comprises:

A.i.1): reaction of the compound (R)-2-[4-methoxy-3-(3-methoxypropoxy)benzyl]-3-methyl-butanal of formula (II) with the beta-ketoester of formula (III) to form the compound of formula (IV):

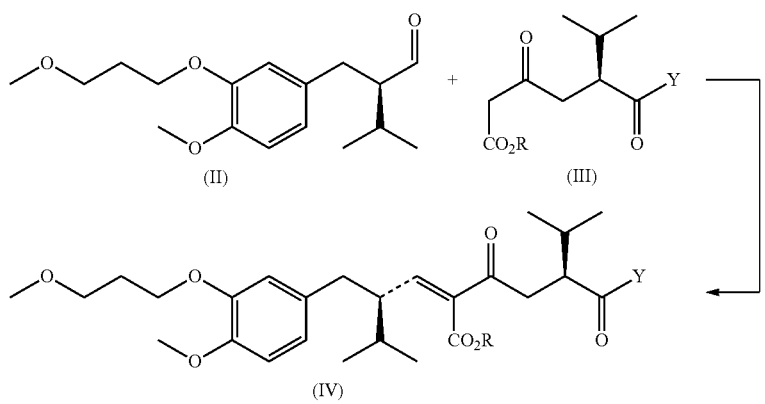

in which R and Y have the meanings given above and the symbol ⌇ in the formula of compound (IV) indicates that the —C=C— double bond can have the E- or Z-configuration;

A.i.2): hydrogenation of the —C=C— double bond of compound (IV) obtained in reaction A.i.1) to form compound (V).

The reaction pathway A.ii) comprises reaction of the derivative of (R)-2-[4-methoxy-3-(3-methoxypropoxy)benzyl]-3-methyl-butyl of formula (II'), in which X represents a leaving group, with the beta-ketoester of formula (III) to form product (V):

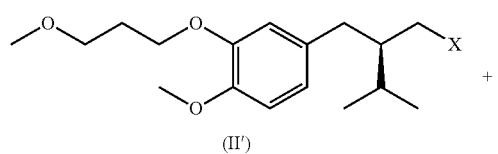

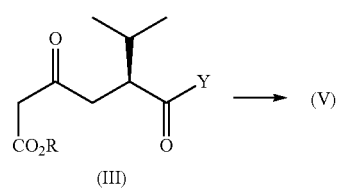

Operation B of the process of the invention, transformation of a compound of formula (V) into an intermediate of formula (VII), can be carried out according to three possible alternative reaction pathways, designated hereunder as B.i), B.ii) and B.iii).

Reaction pathway B.i) comprises:

B.i.1): forming, starting from compound (V), the enol ether of formula (VI):

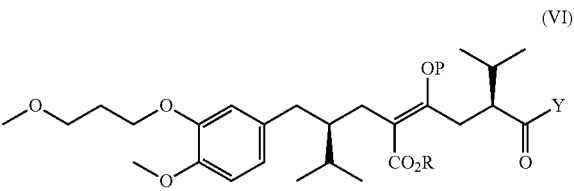

B.i.2): hydrogenating compound (VI) to form compound (VII).

Reaction pathway B.ii) comprises the direct biotransformation of compound (V) into compound (VII).

Finally, reaction pathway B.iii) comprises direct asymmetric hydrogenation of compound (V) to compound (VII).

Once the intermediate of formula (VII) is obtained, this can be transformed, in operation C of the process of the invention, into a cyclic carbamate, (VIII), or into an amino-lactone, (IX").

The transformation of intermediate (VII) into the cyclic carbamate (VIII) takes place according to the reaction pathway C.i), which can be represented schematically as follows:

C.i.1): transformation of intermediate (VII) into an intermediate (VII') by means of one or more reactions of hydrolysis or deprotection of the ester and/or alcoholic group;

C.i.2): transformation of intermediate (VII') into an isocyanate (VII") (optionally isolated); and C.i.3): intramolecular reaction between the alcoholic group and the isocyanate group of compound (VII") to give the cyclic carbamate (VIII):

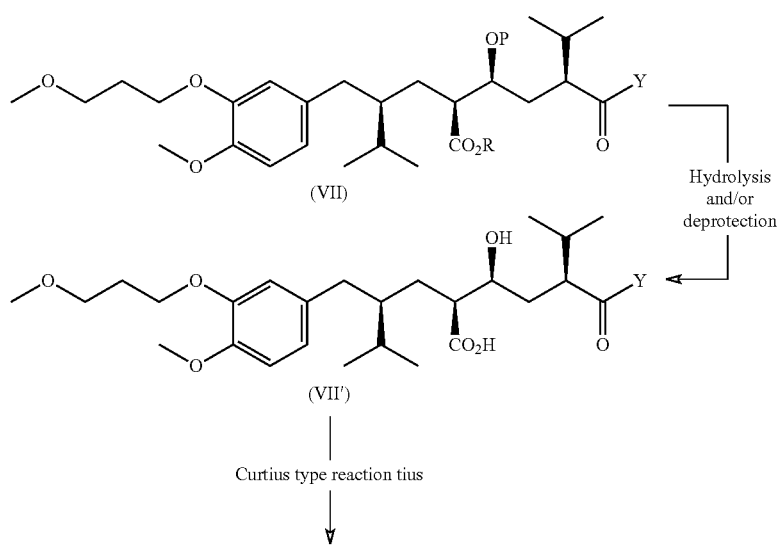

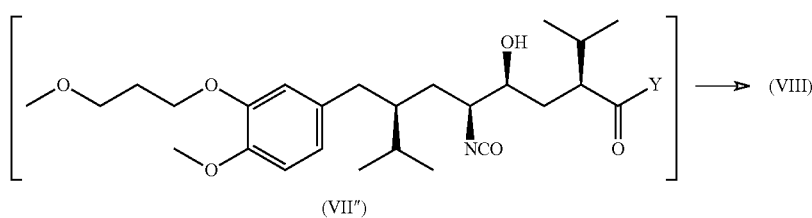

The reactions for transforming compound (VII) into compound (VII') are the typical reactions of hydrolysis or deprotection of esters of carboxylic acids, i.e. basic or acid hydrolysis or hydrogenolysis in the case when the group R is benzyl. These conditions are also suitable in most cases for deprotection of the alcohol function if P is an acyl group, such as acetyl, or a carbamoyl group. In the case when P is a trimethylsilyl group the hydrolytic conditions are sufficient for its removal. In the case when P is a sterically hindered silyl group such as tert-butyldimethylsilyl (TBDMS) or tert-butyldiphenylsilyl (TBDPS) action of the fluoride ion or of hydrogen fluoride is more appropriate.

The transformation of the carboxylic acid (VII') into the isocyanate (VII") which spontaneously undergoes cyclization to give the cyclic carbamate (VIII) is effected by treatment of (VII') for example with diphenylphosphoryl azide (DPPA) of formula $(PhO)_2P(O)N_3$ in an inert solvent, for example toluene, in the presence of an organic base such as a tertiary amine, for example triethylamine and with heating.

However, transformation of intermediate (VII) into the amino-lactone (IX''') can take place according to two routes of synthesis, C.ii) and C.iii).

The first route, C.ii), envisages the following reactions:
C.ii.1): if P is different from H, removal of the protection of the alcohol function as described above;
C.ii.2): lactonization of the alcohol of formula (VII''') catalysed by organic or inorganic acids or bases or induced by a dehydrating agent:

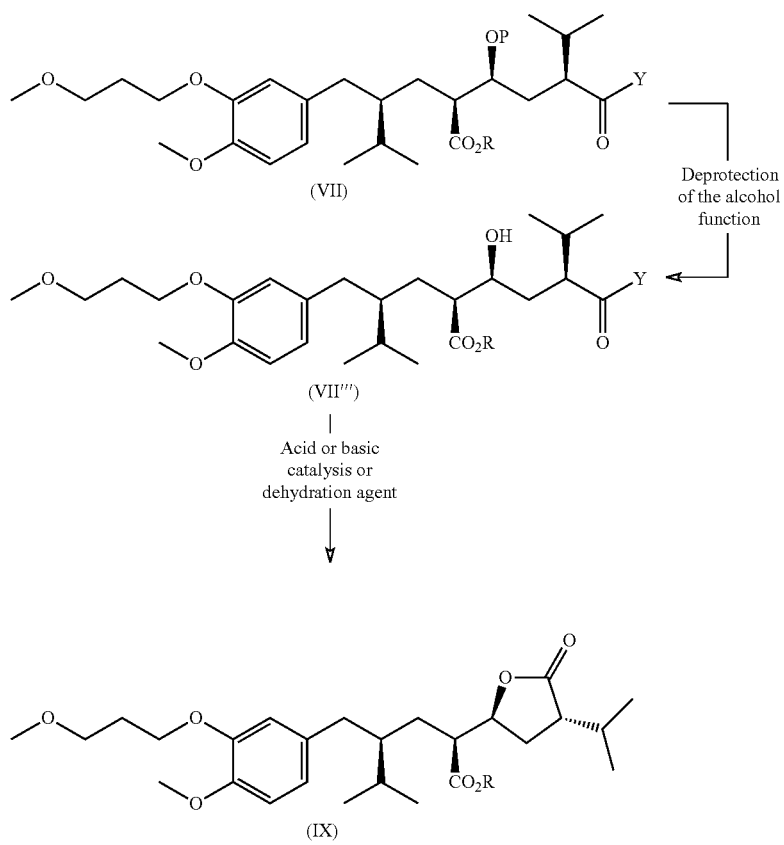

C.ii.3): removal of group R, if different from hydrogen, as described above;

C.ii.4): transformation of the lactone of formula (IX) where R=H into an isocyanate of formula (IX'), which can optionally be isolated, by means of a Curtius reaction as described above and subsequent treatment of (IX') with an alcohol ROH in the presence of an organic base to give the protected amino-lactone (IX"), or direct transformation of (IX) into (IX") by a Curtius reaction in the presence of an alcohol ROH:

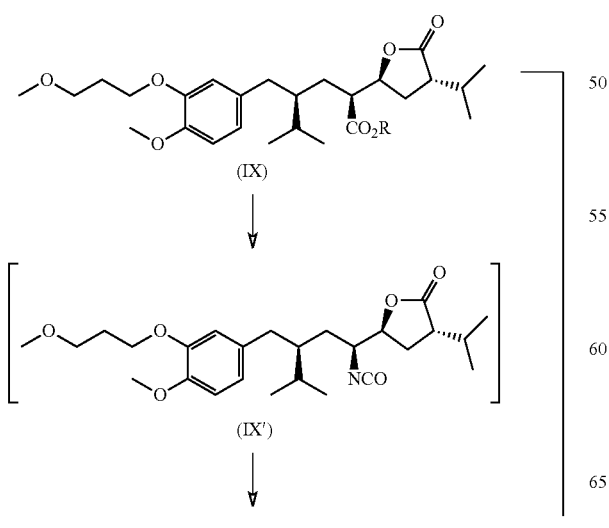

-continued

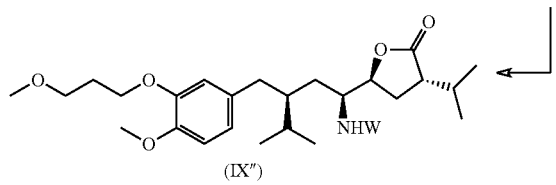

The second route of transformation of the intermediate (VII) into the amino-lactone (IX"), C.iii), envisages the following reactions:

C.iii.1) removal, if present, of the protecting group R on the ester;

C.iii.2) transforming the acid (VII) into the isocyanate (VII'''), which can optionally be isolated, by a Curtius reaction;

C.iii.3) reaction of the isocyanate (VII''') with an alcohol to give a carbamate (VII'''');

C.iii.4) hydrolysis (simultaneous or sequential) of groups P and Y and cyclization of the resultant hydroxy acid to give the lactone (IX")

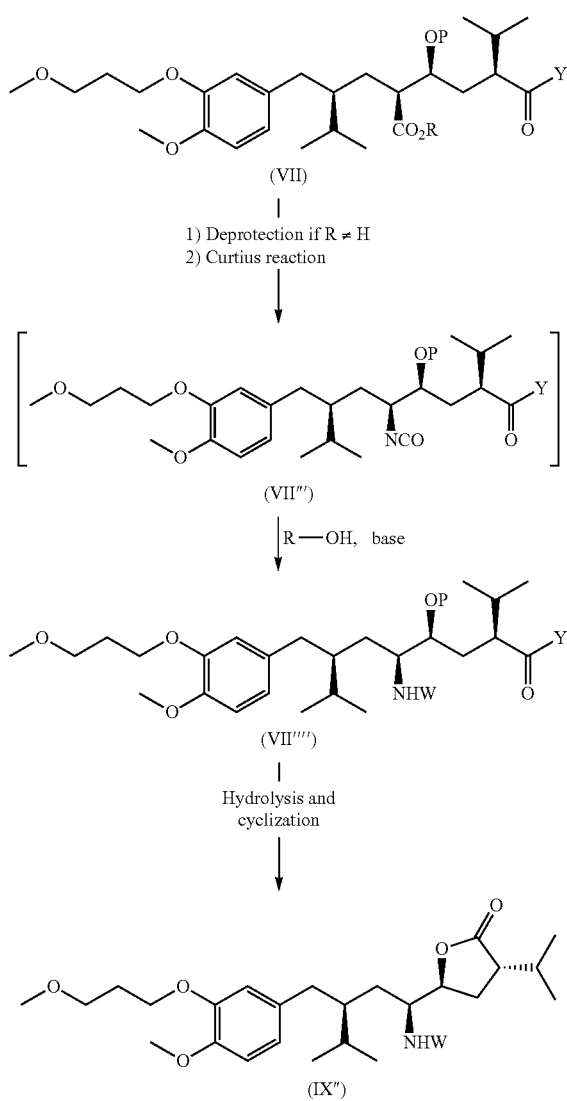

Finally, in the last operation of the process of the invention, D, the cyclic carbamate (VIII) or amino-lactone (IX″) is transformed into the desired product, Aliskiren of formula (I) by reaction with 3-amino-2,2-dimethylpropanamide, of formula:

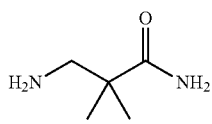

and subsequent hydrolysis of the cyclic carbamate or deprotection of the amino group.

The first part of the synthesis, summarized above as A), comprises formation of the compound of formula (V) according to two possible alternative routes of synthesis, indicated above as A.i) and A.ii), which have in common the use of the compounds of general formula (III), homochiral isopropyl-substituted beta-ketoesters; these compounds are novel and constitute a second aspect of the invention.

The compounds (II) and (II′) that are reacted with (III) respectively in the routes of synthesis A.i) and A.ii) can be prepared starting from compounds of general formula (X):

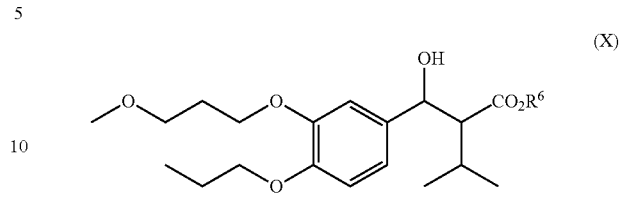

In the above formula, $R^6$ is an alkyl or haloalkyl group, for example methyl, ethyl, propyl, butyl or 2,2,2-trifluoroethyl. The preparation of compounds of type (X) is known from patent EP 1,296,912 B1.

Compound (X) can easily be dehydrated with acid catalysis by removal of the —OH group in the benzylic position, owing to the stability of the double bond conjugated with the phenyl that is derived from it; it is possible for example to work in toluene or in xylene under reflux, using a strong organic or mineral acid such as camphorsulphonic or para-toluenesulphonic acid or sulphuric acid; the result of dehydration is compound (XI):

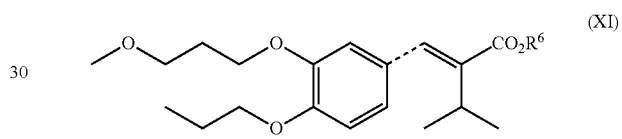

in which the symbol ⌇ indicates that the double bond can have the E or Z configuration. Compound (XI) is then hydrogenated according to known procedures with a heterogeneous catalyst based on a transition metal such as nickel, palladium or platinum, for example Raney nickel, palladium on carbon, platinum on carbon, supplying compound (XII):

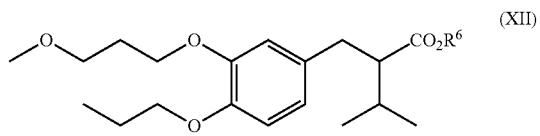

The ester group of compound (XII) is then hydrolysed enzymatically to supply the corresponding acid. In this step of the synthesis, the chiral centre in the a position relative to the carboxyl carbon is produced selectively, obtaining (R)-2-[4-methoxy-3-(3-methoxypropoxy)benzyl]-3-methyl-butanoic acid of formula (XIII):

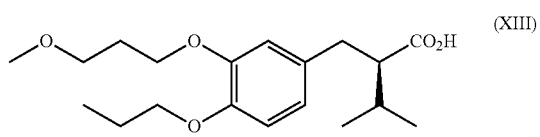 [SMILES: CCCOc1ccc(C[C@@H](C(=O)O)C(C)C)cc1OCCCOC]

The formation of the chiral centre is also described in two alternative routes of synthesis of compound (XIII) given in the cited patent EP 1,296,912 B1 and in patent application WO 02/02500 A1, which employ for this step, respectively, intermediate formation of the allyl alcohol with diisobutyl aluminium hydride (Dibal-H), a pyrophoric reagent, and subsequent asymmetric reduction, or direct asymmetric hydrogenation with a catalyst based on rhodium and chiral phosphines.

In the case of the invention, compound (XIII) is produced starting from compound (XII) by enzymatic hydrolysis. For this operation, animal liver extracts are used, in particular "Pig Liver Esterase" (PLE); or animal liver powders dehydrated with acetone (generally known in this field as "liver acetone powder"), such as "sheep liver acetone powder" (SLAP), "bovine liver acetone powder" (BLAP) and, preferred for the purposes of the invention, "horse liver acetone powder" (HLAP). Enzymatic hydrolysis is performed with a substrate that is preferably a compound of formula (XII) in which R is n-butyl, at a concentration between 10 and 1000 mM, and preferably between about 90 and 100 mM; at a temperature between room temperature and about 50° C., and preferably of about 40° C.; and in a buffered water-based solvent at a pH between about 5 and 9, for example a phosphate-based buffer, or preferably in a tris(hydroxymethyl)aminomethane/HCl buffer system maintained at a pH of about 7.5; it is also possible to work in the presence of a co-solvent, selected for example from methanol (MeOH), ethanol (EtOH), tert-butanol (t-BuOH), tetrahydrofuran (THF), dimethylformamide (DMF), acetone, acetonitrile, di-isopropyl ether (i-Pr$_2$O) and dimethylsulphoxide (DMSO), but preferably hydrolysis is carried out without adding a co-solvent.

The enzymatic transformation from compound (XII) to compound (XIII) according to the invention has some advantages relative to the corresponding reactions given in documents EP 1,296,912 B1 and WO 02/02500 A1 cited above. Firstly, the reaction takes place in mild conditions (for example, pH 7.5 and at 40° C.), with good conversion yield (about 40% against a theoretical 50%) and with enantiomeric excesses of about 96-97%, comparable or better than those obtainable with enantioselective hydrogenations; moreover, the unhydrolysed ester can easily be recovered and racemized, for reuse in the same reaction, thus increasing the overall yield of the desired product.

The acid (XIII) is then reduced with hydrides, for example with lithium aluminium hydride, LiAlH$_4$, to the corresponding alcohol, (XIV):

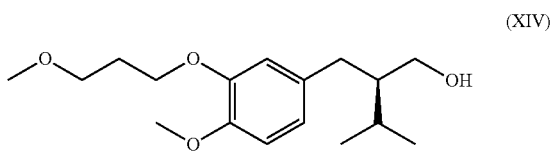 [SMILES: COCCCOc1cc(C[C@@H](CO)C(C)C)ccc1OC]

(XIV)

The alcohol (XIV) can then be submitted to controlled oxidation to supply the aldehyde (II), the reagent of A.i.1); or can be halogenated or activated to supply a compound of formula (II'), the reagent of A.ii.1).

For oxidation to supply the aldehyde (II), it is possible (in particular for preparative work on a laboratory scale) to employ known techniques, such as Swern oxidation and variants thereof, or to use well-known iodine-based oxidizing agents such as the Dess-Martin reagent or iodoxybenzoic acid (IBX); when working on an industrial scale, it is preferable to employ methods that make use of sodium hypochlorite or N-chloroimides such as N-chlorosuccinimide in conjunction with a radical catalyst such as the 2,2,6,6-tetramethylpiperidinyl-N-oxyl radical (known by the abbreviation TEMPO).

In the case when, in the compound of formula (II'), the leaving group is a halogen, said compound can be obtained by reacting an alkaline halide such as sodium or potassium bromide or iodide with the activated derivative, for example by reacting the mesylate or tosylate with sodium iodide in an aprotic dipolar solvent such as dimethylformamide or dimethylacetamide or acetonitrile or methyl ethyl ketone. Halogenation can also be performed directly on alcohol (XIV) by reaction for example with bromine or iodine in the presence of a stoichiometric amount of a phosphine such as triphenyl phosphine and an organic base such as triethylamine or imidazole. The iodo-derivative is particularly useful for the purposes of synthesis of Aliskiren. Alternatively, in the compound of formula (II'), the leaving group can be a sulphonate such as methanesulphonate (mesylate), trifluoromethanesulphonate (triflate) or, preferably, paratoluenesulphonate (tosylate); these derivatives are prepared starting from alcohols (such as the compound of formula (XIV)) by techniques that are well known.

In its turn, compound (III), used in reactions A.i.1) or A.ii.1), can be prepared as described below.

The first step in the preparation comprises reaction between 3-methylbutanoyl chloride and an Evans homochiral oxazolidinone (chiral auxiliary), in particular the oxazolidinone derived from (S)-phenylalaninol in an inert solvent such as dichloromethane or more conveniently acetonitrile in the presence of an inorganic base such as an alkaline carbonate or an organic base such as a tertiary amine, for example triethylamine optionally in the presence of a catalyst of the acylation reaction such as 4-dimethylaminopyridine (DMAP), at a temperature between 0 and 5° C., with formation of an intermediate of type (XV):

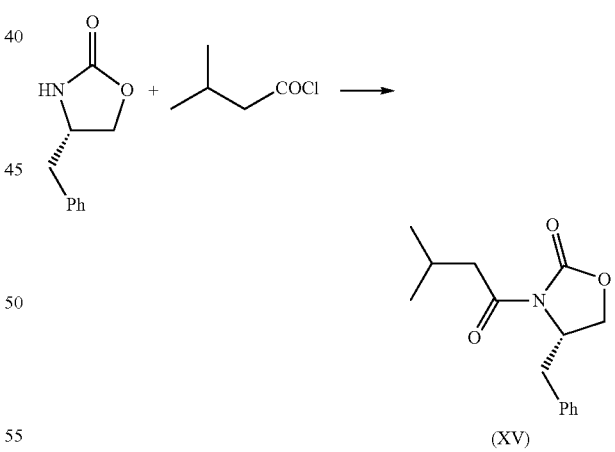

(XV)

Both the Evans chiral auxiliaries and the acyl chloride are commercially available compounds.

The intermediate (XV) is treated, in an aprotic solvent (preferably THF) and at low temperature (for example, −40° C.), with a strong base, for example lithium diisopropylamide (LDA) or lithium, sodium or potassium bis(trimethylsilyl)amide (LiHMDS, NaHMDS or KHMDS); next, an α-halide of an ester of acetic acid, of general formula X—CH$_2$—COOZ, in which Z can be for example benzyl or tert-butyl, is added to the solution, forming the intermediate (XVI):

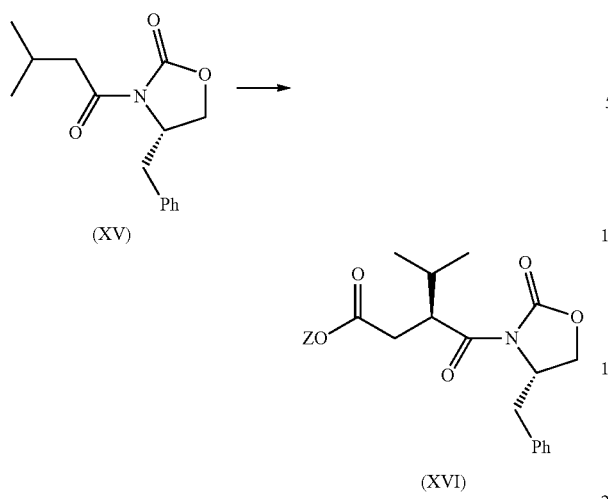

The intermediate (XVI) is then deprotected by removing the group Z, to give the corresponding acid, the intermediate (XVI'):

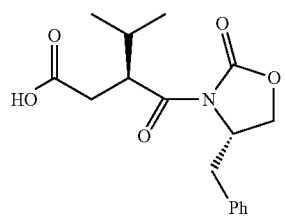

Deprotection can take place by hydrogenolysis, for example with gaseous hydrogen in the presence of a catalyst based on transition metals supported on an inert matrix, for example palladium on carbon, in the case when Z is benzyl, or by means of strong acids, such as formic, hydrochloric or trifluoroacetic acid, in the case when Z is tert-butyl.

The intermediate (XVI') is finally activated first with carbonyl diimidazole, and then reacted with a magnesium salt of a monoester of malonic acid of general formula ($R^1OC(O)$—$CH_2$—$COO^-$)·½$Mg^{2+}$, in which $R^1$ is a $C_1$-$C_6$ alkyl or benzyl according to the Masamune homologation reaction; the result of the reaction is the desired compound (III).

Use of the Evans auxiliary provides perfect control of the stereochemistry of the intermediate (XVI) and consequently in the final product (III); no traces of the diastereoisomer are observed by HPLC and $^1$H NMR. Moreover, all of the intermediates in the synthesis of (III) presented above are crystalline solids that can be purified easily, apart from product (III) itself, which is oily, but is obtained in pure form by solvent extraction and washing with water. Finally, all the reactions for synthesis of (III) use commercially available reagents and take place with good yields, without requiring the use of special reactors or very low temperatures.

If desired, the chiral auxiliary in the intermediate (XVI) can be replaced with a benzyloxy group by reaction with the lithium salt of benzyl alcohol. In its turn, the benzyl group thus introduced can be removed by hydrogenolysis and the acid obtained can be converted into the ester of interest, for example methyl, ethyl, isopropyl, tert-butyl, cyclohexyl ester. In this case the synthesis scheme of compound (III) can be summarized as follows:

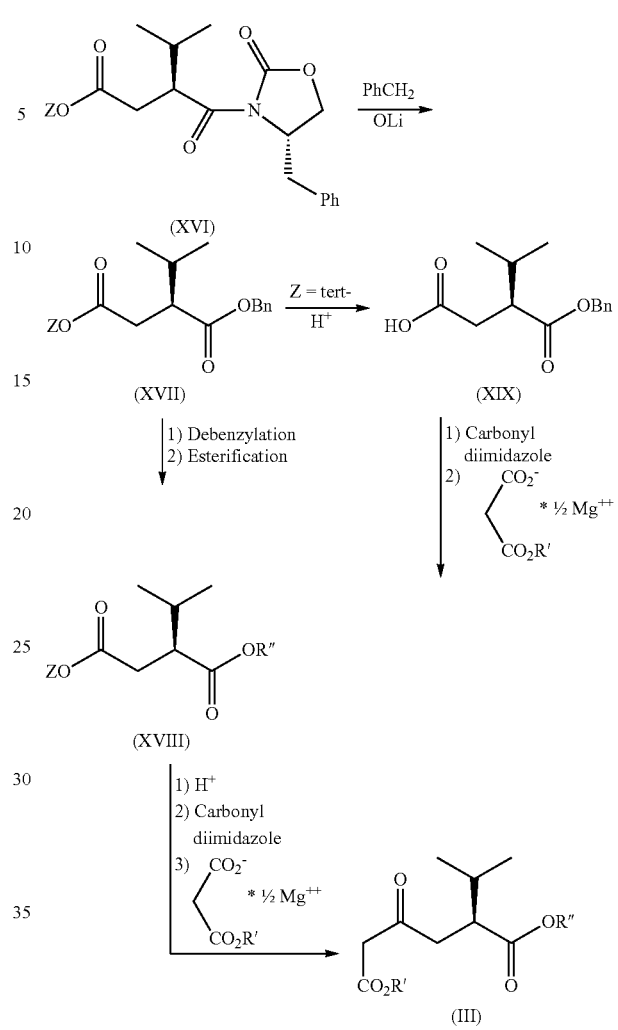

In formula (III) given above, both R' and R" can be alkyl or benzyl.

Compound (V) can be obtained by hydrogenation of the C=C double bond of compound (IV). Hydrogenation is carried out using palladium on carbon or on another inert matrix such as silica or alumina, preferably carbon, as catalysts. It is also possible to use palladium hydroxide supported on carbon, platinum on carbon or platinum oxide, preferably platinum oxide or Raney nickel.

The hydrogenation reaction is carried out in an inert solvent such as tetrahydrofuran or ethyl acetate, preferably in tetrahydrofuran, with hydrogen at ambient pressure or at a pressure between 1 and 10 bar, preferably at ambient pressure.

Compound (IV) is obtained by Knoevenagel reaction of the aldehyde (II) and of the beta-ketoester (III), dissolving both reactants in a polar aprotic solvent such as dimethylacetamide or dimethylformamide or in an apolar aprotic solvent such as toluene and using piperidine, morpholine or pyridine as catalyst, preferably piperidine optionally together with an equal stoichiometric amount of an organic acid such as acetic acid or benzoic acid. The reaction can be carried out at a temperature between about 20 and 50° C., preferably about 25° C.

The reaction between (II) and (III) can also be carried out using the Lehnert modification of the Knoevenagel reaction, i.e. using a stoichiometric amount of titanium tetrachloride and of pyridine in an inert solvent such as dichloromethane at a temperature between −20 and 20° C., preferably at 0° C.

Compound (V) can also be obtained directly by C-alkylation of the beta-ketoester (III) with an activated derivative (II').

The reaction takes place in a polar aprotic solvent such as dimethylformamide, dimethylacetamide, tetrahydrofuran or preferably acetonitrile, or in a polar protic solvent such as tert-butanol, in the presence of a base; the base can be inorganic, such as a carbonate of an alkali metal or alkaline-earth metal such as sodium carbonate, potassium carbonate, caesium carbonate or calcium carbonate, preferably sodium or potassium carbonate; or an organic base, such as an alcoholate of lithium, of sodium or of potassium, preferably tert-butylate of sodium or of potassium.

The reaction can be carried out at temperatures between about 20° C. and the reflux temperature of the solvent, preferably between 40° C. and 60° C.

The compound of formula (V) is converted to the enol ether (VI) by treatment of (V) with an acylating agent such as acetic anhydride or a silylating agent such as trimethylsilyl chloride, and an organic or inorganic base, preferably a tertiary amine, optionally in an inert solvent such as dichloromethane or toluene.

If desired, the group R of the enol ether (VI) can be removed in various conditions depending on its nature: in acid conditions when R=tert-butyl or in conditions of hydrogenolysis when R=benzyl as described above for the preparation of compound (XVI').

The stereoselective hydrogenation of an enol derivative of formula (VI) to give a compound of formula (VII) is carried out using a catalyst based on a transition metal such as ruthenium, rhodium, iridium, nickel, palladium, platinum or salts thereof, optionally mixed, and optionally supported on an inert matrix such as carbon, silica or alumina or on an organic polymer matrix. Preferably the transition metal is used in the form of a complex that is soluble in the reaction medium optionally coordinated with an achiral or chiral mono- or bidentate phosphine. In the case of chiral phosphines, these can be used as a racemic mixture, in enantiomerically enriched form or in the form of a single enantiomer. Homogeneous catalysts of rhodium or ruthenium or iridium coordinated with bidentate phosphines such as TCFP, PhanePhos, Binap, DiPFc, BoPhoz and DCPF are particularly preferred.

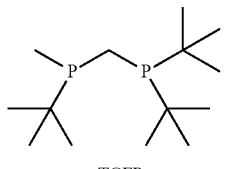

rac-TCFP

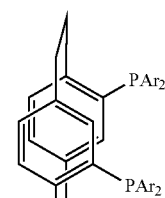

rac-PhanePhos

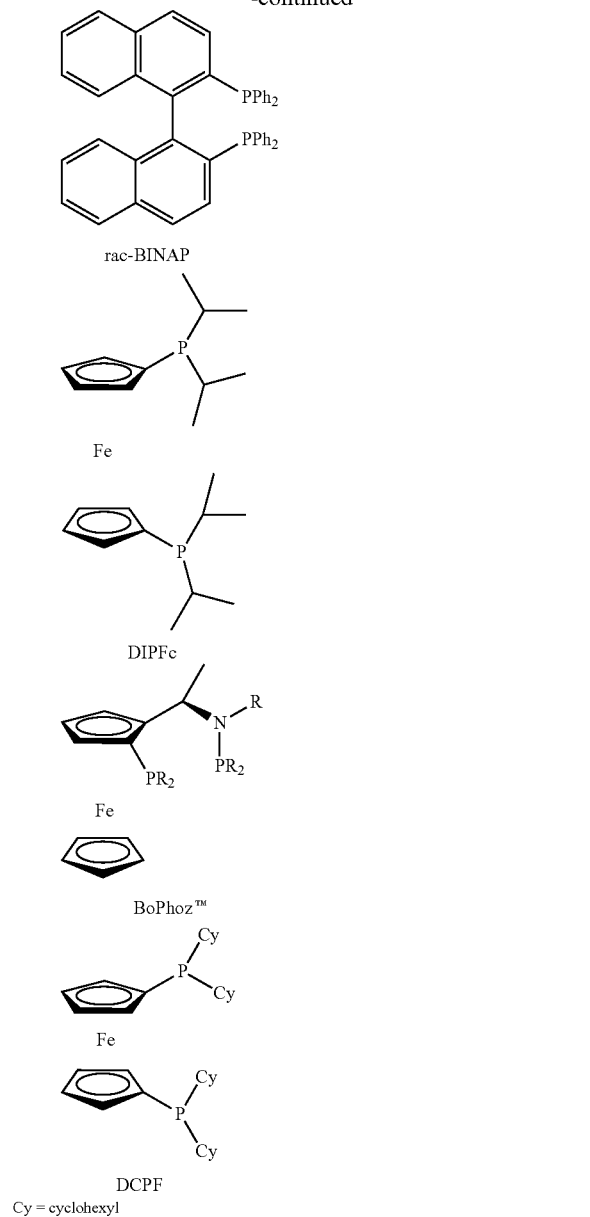

Cy = cyclohexyl

In the case when, in the enol compound (VI), R=hydrogen, it is also possible to use a salt of the compound, in particular its salts of alkali metals or alkaline earth metals or of amines, preferably tertiary alkyl amines such as triethylamine. Using the enol derivative (VI) in the form of a salt of a tertiary amine makes the hydrogenation reaction particularly stereoselective, making it possible to obtain diastereomeric excesses above 95%, and to use smaller amounts of catalyst and shorter reaction times.

The optimum conditions for the reaction of hydrogenation of an enol derivative of formula (VI) envisage the use of a catalyst of rhodium (I), which can be achiral, such as [Rh(DiPFc)(cod)]BF$_4$, or preferably chiral, such as [((S)-PhanePhos)Rh(cod)]BF$_4$; or catalysts of ruthenium (II) such as [Ru(R-Binap)(benzene)Cl]Cl in halogenated solvents such as 1,2-dichloroethane or, preferably, dichloromethane, or alcohols such as methanol, isopropanol, or preferably ethanol, at a temperature between 40 and 80° C., preferably about 60° C., at a hydrogen pressure between 5 and 30 bar, preferably about 30 bar. Preferred substrates for carrying out the hydrogenation reaction are those in which R=H, i.e. free acids. The reaction is preferably carried out in the presence of an aliphatic tertiary amine such as ethyl-diisopropylamine or, preferably, triethylamine, in a molar ratio between 0.5 and 1 (preferably 0.7) with the enol derivative of formula (VI).

The formation of the salt with the tertiary amine can take place directly in the reaction medium. The molar ratio of catalyst to substrate is from 1/10000 to 1/100, preferably 1/1000.

The beta-ketoesters of formula (V) can also be hydrogenated directly to give beta-hydroxy esters of formula (VII) where P=H (reaction pathway B.iii) according to the procedures for enantioselective hydrogenation developed by Noyori, i.e. using homogeneous catalysts mainly based on Ru(II) and bidentate chiral phosphines. This technology provides controlled formation of two stereocentres when the beta-ketoester has a labile stereocentre in the alpha position by a process of dynamic kinetic resolution.

The following are examples of chiral phosphines that are particularly suitable for the use described above (only one enantiomer is shown):

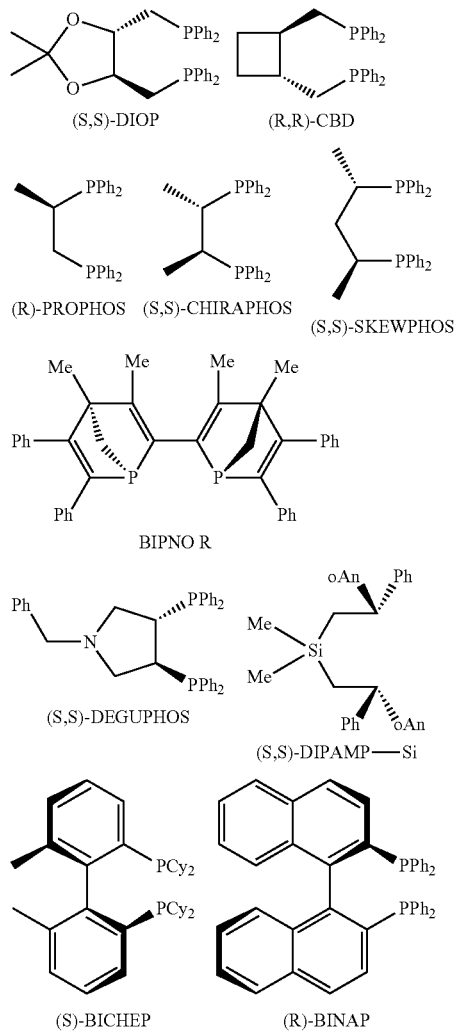

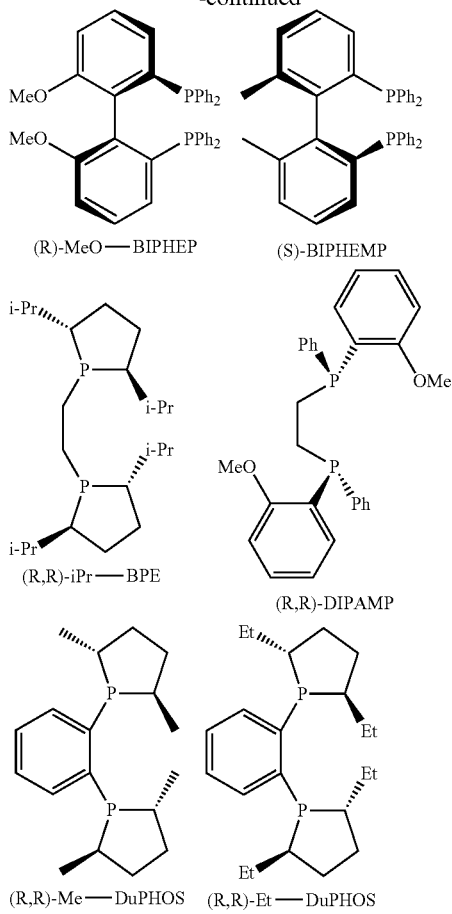

Alternatively the beta-ketoesters of formula (V) can be reduced to beta-hydroxyesters of formula (VII) in which P=H by the use of enzymes or microorganisms with ketoreductase activity, in the presence of a cofactor such as NAD for example and optionally in the presence of a system able to regenerate the cofactor.

The compound of formula (VII) in which R=H is then converted to the isocyanate of formula (VII''') by means of a Curtius reaction that comprises:
  activation of the carboxyl function of the acid (VII) by means of a mixed anhydride, for example by reaction with a chloroformate such as ethyl or isobutyl chloroformate, or with the chloride of an acid, for example pivaloyl chloride, in the presence of an organic base such as a tertiary amine in an inert solvent; or by formation of an acyl chloride by treating the acid (VII) with oxalyl chloride or thionyl chloride or by transformation into any other activated derivative of a carboxylic acid;
  reaction of the activated derivative of the acid with sodium or potassium azide, forming an acylazide (optionally isolated);
  rearrangement of the acylazide to the isocyanate (VII''') by heating.

This reaction of transformation of the acid (VII) into the isocyanate (VII''') can be carried out in a single operation by treatment with diphenyl phosphoryl azide $(PhO)_2P(O)N_3$ in an inert solvent such as toluene, by heating and in the presence of a tertiary amine.

The isocyanate (VII'''), which can optionally be isolated, is then treated with an alcohol R—OH where R is as defined above (R=tert-butyl, benzyl, cyclohexyl, allyl and 2,2,2-trichloroethyl are particularly preferred) in the presence of an organic base such as a tertiary amine, optionally in an inert solvent such as toluene or tetrahydrofuran and by heating, obtaining the carbamate.

The carbamate (VII'''') is then submitted to acid hydrolysis to detach the protecting group P on the alcohol function and to hydrolyse group Y: the hydroxy acid thus obtained undergoes cyclization spontaneously to give the lactone (IX''). Suitable conditions for acid hydrolysis are strong mineral or organic acids, if desired in aqueous solution, such as hydrochloric or sulphuric or formic or para-toluenesulphonic acid mixed with water-miscible alcoholic solvents such as methanol, ethanol, isopropanol. It is also possible to use acid resins such as Dowex or Nafion. The reaction of acid hydrolysis and cyclization is carried out at a temperature between 50° C. and the reflux temperature of the solvent.

The last step in the synthesis, i.e. conversion of the lactone (IX'') to Aliskiren, takes place according to methods that are known by a person skilled in the art; see for example patent EP 687,503 B1, or the articles "*Total Synthesis of "Aliskiren": The First Renin Inhibitor in Clinical Practice for Hypertension*", S. Hanessian et al., *Organic Letters,* 2010, 12 (8), p. 1816-1819 and "*Amide Bond Formation via Reversible, Carboxylic Acid-Promoted Lactone Aminolysis*", M. A. Foley and T. F. Jamison, *Organic Process Research & Development* 2010, 14 (5), p. 1177-1181. The invention will be further illustrated by means of the following examples.

EXAMPLE 1

Preparation of butyl-2-(4-methoxy-3-(3-methoxypropoxy)benzyl)-3-methylbutanoate, Compound of Formula (XII) in which $R^6$ is the Butyl Radical

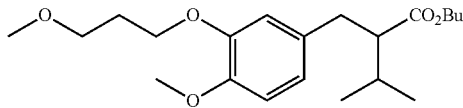

A 250-ml jacketed reactor is charged, under nitrogen atmosphere, with 86.1 ml of a 0.72 M solution of lithium diisopropylamide in THF, heptane and ethylbenzene, equal to 62.0 mmol of the base. The solution is cooled to –40° C., and 15 ml of a solution of butyl isovalerate in anhydrous THF, containing 8.16 g (51.5 mmol) of the ester, are added slowly, in 30 minutes. The solution is stirred for 30 minutes, after which a solution obtained by dissolving 9.7 g (43.2 mmol) of 4-methoxy-3-(3-methoxypropoxy)benzaldehyde in 15 ml of anhydrous THF is added slowly, in 45 minutes. The solution is stirred at –40° C. for 1.5 h, after which the reaction is stopped by adding 40 ml of a saturated aqueous solution of ammonium chloride.

The phases are separated and the aqueous phase is extracted with 140 ml of ethyl acetate; the organic phases are combined and washed successively with 80 ml of 0.5N HCl, 80 ml of water and 80 ml of aqueous solution of NaCl. The organic phase extracted is dried over sodium sulphate, filtered and concentrated to constant residue at reduced pressure. The resultant oil is crystallized from hexane, giving 13.0 g of the hydroxyl ester of formula (IX) in the form of a colourless solid, at a yield of 79%.

The product thus obtained is dissolved in 100 ml of toluene, 850 mg of camphorsulphonic acid are added (in a ratio of 9.3 mol. % relative to the mols of ester to be dehydrated), the mixture is heated under reflux and the water is separated in a Dean-Stark system. The reaction is monitored by TLC, using a hexane:ethyl acetate 6:4 mixture as eluent. On completion of reaction the mixture is cooled to room temperature and washed twice with 50 ml of a 5% (w/v) sodium bicarbonate solution. The organic phase is concentrated to dryness giving the anhydrous product of formula (X) in quantitative yield.

Compound (X) is submitted to catalytic hydrogenation in methanol (120 ml) with Pd/C at 10% (1 mol. %) at room temperature, working with ambient pressure of hydrogen; this operation takes 18 hours.

After filtration of the catalyst and removal of the methanol at reduced pressure, 11.5 g of the product to be prepared are obtained, equal to a yield of 92%, in the form of a yellowish oil.

$^1$H NMR (300 MHz, $CDCl_3$, 298K) 6.73-6.69 (m, 3H), 4.09 (t, J=6.4 Hz, 2H), 3.93 (t, J=6.7 Hz, 2H), 3.81 (s, 3H), 3.57 (t, J=6.4 Hz, 2H), 3.34 (s, 3H), 2.77 (d, J=7.6 Hz, 2H), 2.41 (q, J=7.0 Hz, 1H), 2.08 (quin, J=6.4 Hz, 2H), 1.47-1.43 (m, 2H), 1.28-1.18 (m, 2H), 1.01 (d, 6.7 Hz, 3H), 0.96 (d, 6.7 Hz, 3H), 0.84 (t, J=7.3 Hz, 3H).

EXAMPLE 2

Enzymatic Hydrolysis of Compound (XII) to Supply the Compound of Formula (XIII), (R)-2-[4-methoxy-3-(3-methoxypropoxy)benzyl]-3-methylbutanoic acid A 100-ml flask equipped with an efficient magnetic stirrer is charged with 1.134 g of methyl-2-(4-methoxy-3-(3-methoxypropoxy)benzyl)-3-methylbutanoate (3.5 mmol) obtained by saponification and esterification with methanol of the butyl ester obtained in the preceding example; then 85 ml of a 0.3 M buffer solution of tris(hydroxymethyl)aminomethane/HCl with pH 7.5 are added. The mixture is stirred at high speed producing a finely dispersed suspension. 1.750 g of HLAP (Aldrich) are added; the flask is stoppered and immersed in a thermostatic bath at 40° C., and the suspension is stirred rapidly for 48 hours, monitoring the progress of the reaction by TLC (eluent hexane:ethyl acetate 8:2 mixture containing 3% of acetic acid; $R_f$ ester=0.34, $R_f$ acid=0.2; visualization after development with cerium ammonium molybdate). The mixture is cooled to room temperature and the pH is adjusted to 3.5 by adding 0.5 M solution of citric acid. After adding 10 ml of ethyl ether, the aqueous phase is saturated with NaCl and the mixture is stirred vigorously for 10 min, then filtered on Celite and washed with an ethyl ether:methanol 9:1 mixture.

The filtrate is transferred to a reparatory funnel, the phases are separated and the aqueous phase is re-extracted with ethyl ether.

The organic phases are combined and dried over sodium sulphate, then concentrated until a residue is obtained, which is purified by flash chromatography with a hexane:ethyl acetate elution gradient from 7:3 to 0:10.

521 mg of acid are obtained, which is esterified with diazomethane and analysed by HPLC, showing an enantiomeric excess (e.e.) of 83.3%. The ester (475 mg) is analysed in its turn by HPLC, showing e.e. of 95.0%. The HPLC analyses are carried out in the following conditions:
  column: Chiralpak AD 250×4.6 mm;
  flow rate: 1 ml/min;
  injected volume: 10 µl;
  detector wavelength: 210 nm;
  column temperature: RT;
  isocratic mobile phase, 95% hexane, 5% ethanol, 0.1% trifluoroacetic acid;
  retention times: (S)-(−)-acid 11.17 min, (R)-(+)-acid 13.03 min.

The degree of conversion (evaluated with $^1$H NMR) is equal to 50.6%. The enantioselectivity, E, of the mixture is also measured, and is found to be 40.3. The enantioselectivity is defined as:

$$E = \ln\{(1-ee_s)(ee_p)/ee_s + ee_p\}/\ln\{(1+ee_s)(ee_p)/ee_s + ee_p\}$$

The procedure of this example is repeated on ethyl-2-(4-methoxy-3-(3-methoxypropoxy)benzyl)-3-methylbutanoate and n-butyl-2-(4-methoxy-3-(3-methoxypropoxy)benzyl)-3-methylbutanoate, giving the following results:

|  | From ethyl ester | From n-butyl ester |
|---|---|---|
| e.e. acid (%) | 95.6 | 96.2 |
| e.e. ester (%) | 70.0 | 87.0 |
| conversion $^1$H NMR (%) | 38.9 | 44.9 |
| E | 93.4 | 147.4 |

The enantiomeric excess increased to values above 99.5% by formation of the ammonium salt in isopropanol, filtration, hydrolysis with dilute HCl and extraction with toluene.

EXAMPLE 3

Preparation of (R)-2-[4-methoxy-3-(3-methoxypropoxy)benzyl]-3-methylbutanol, Compound (XIV)

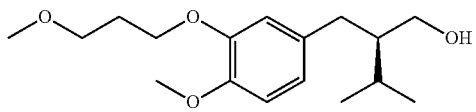 [SMILES: COCCCOc1cc(C[C@@H](CO)C(C)C)ccc1OC]

A 100-ml flask is charged under inert atmosphere (nitrogen) with 500 mg (13.18 mmol) of lithium aluminium hydride and 15 ml of THF. The suspension is heated to 40° C., and 2.045 g (6.59 mmol) of (R)-2-[4-methoxy-3-(3-methoxypropoxy)benzyl]-3-methyl-butanoic acid dissolved in 5 ml of THF are added. The mixture is maintained at 40° C. and stirred for two hours, monitoring the course of the reaction by TLC (ethyl acetate:mixture of hexanes 7:3; $R_f$ acid=0.5; $R_f$ alcohol=0.6; spot detecting system with potassium permanganate and UV at 254 nm). At the end of reaction the mixture is cooled to room temperature and 0.5 ml of water, 0.5 ml of a 15% w/w solution of NaOH and another 0.5 ml of water are added dropwise. The mixture is diluted with toluene, filtered on Celite and concentrated to constant residue, obtaining 1.90 g (yield 97%) of product in the form of a colourless dense oil.

$^1$H NMR (300 MHz, CDCl$_3$, 298K) 6.79-6.72 (m, 3H), 4.09 (t, J=6.4 Hz, 2H), 3.82 (s, 3H), 3.58-3.55 (m, 4H), 3.35 (s, 3H), 2.62 (dd, J=13.8, 5.5 Hz, 1H), 2.45 (dd, J=13.8, 9.8 Hz, 1H), 2.09 (quin, J=6.4 Hz, 2H), 1.90-1.75 (m, 1H), 1.70-1.55 (m, 1H), 1.02 (d, J=3.1 Hz, 3H), 1.00 (d, J=3.1 Hz, 3H).

$^{13}$C NMR (75 MHz, CDCl$_3$, 298K) δ 149.9, 149.2, 135.7, 122.8, 115.9, 113.4, 71.0, 67.6, 64.4, 60.2, 57.6, 50.3, 35.6, 31.1, 29.4, 21.1

The mixture is analysed by HPLC to determine its enantiomeric excess, working in the same conditions as the preceding example, with retention times: (S)-(−)-alcohol 18.39 min, (R)-(+)-alcohol 20.21 min; value of e.e. is found to be above 99.5%.

EXAMPLE 4A

Preparation of (R)-2-[4-methoxy-3-(3-methoxypropoxy)benzyl]-3-methylbutanal, Compound (II)

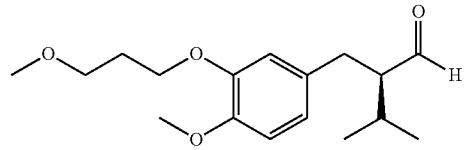 [SMILES: COCCCOc1cc(C[C@@H](C=O)C(C)C)ccc1OC]

A 25-ml flask equipped with a magnetic stirrer is charged with 309 mg (1.043 mmol) of compound (XIV) of the preceding example, 5 ml of dichloromethane, 5 ml of an aqueous solution of concentration 0.5 M of NaHCO$_3$ and 0.05 M of K$_2$CO$_3$, 16.3 mg (0.1043 mmol) of TEMPO free radical and 29 mg of tetrabutylammonium chloride (0.1043 mmol). The two-phase mixture is stirred at the maximum speed of the magnetic stirrer and 200 mg (1.49 mmol) of N-chlorosuccinimide are added in a single portion. The reddish mixture is stirred vigorously at RT for three hours, monitoring the course of the reaction by TLC (mixture ethyl acetate:hexanes 7:3; $R_f$ alcohol=0.6; $R_f$ aldehyde=0.84; development KMnO$_4$ and UV) until the alcohol has disappeared.

The mixture is diluted with 20 ml of dichloromethane and 20 ml of water, the phases are separated and the organic phase is washed with 10 ml of brine, dried over sodium sulphate and concentrated to constant residue, obtaining 279 mg of product as dense yellow oil (yield 91%).

$^1$H NMR (300 MHz, CDCl$_3$, 298K) 9.66 (d, J=2.8 Hz, 1H), 6.76-6.66 (m, 3H), 4.07 (t, J=6.4 Hz, 2H), 3.82 (s, 3H), 3.56 (t, J=6.2 Hz, 2H), 3.36 (s, 3H), 2.90 (dd, J=14.1, 9.2 Hz, 1H), 2.68 (dd, J=14.0, 4.9 Hz, 1H), 2.48-2.43 (m, 1H) 2.12-2.03 (m, 3H), 1.02 (d, J=3.1 Hz, 3H), 1.00 (d, J=3.1 Hz, 3H).

$^{13}$C NMR (75 MHz, CDCl$_3$, 298K) δ 206.7, 150.0, 149.5, 133.8, 122.6, 115.7, 113.5, 70.9, 67.6, 61.3, 60.2, 57.6, 33.3, 31.1, 30.0, 21.5, 21.3.

It is not possible to separate the enantiomers of the product by HPLC. To verify that racemization did not occur during the reaction, a portion of the aldehyde is reduced to alcohol with sodium borohydride in methanol and analysed; an enantiomeric excess greater than 99.5% is found.

EXAMPLE 4B

Preparation of (R)-4-(2-(iodomethyl)-3-methylbutyl)-1-methoxy-2-(methoxypropoxy)benzene, Compound of Formula (II') in which X=I

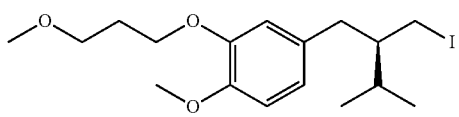 [SMILES: COCCCOc1cc(C[C@@H](CI)C(C)C)ccc1OC]

A 50-mL flask is charged with the alcohol obtained in Example 3 (3.15 g, 10.6 mmol), toluene (15 ml), triethylamine (1.64 ml, 11.7 mmol); the system is cooled to 0° C. under nitrogen and mesyl chloride is added dropwise (867 μl, 11.1 mmol). After addition, it is stirred at 20° C. for 1.5 hours, then water is added (10 ml), the phases are separated, the organic phase is washed with brine (5 ml), it is dried over sodium sulphate and is evaporated to dryness. The mesylate is taken up in acetonitrile (20 ml) and sodium iodide is added (4.50 g, 30 mmol) and it is heated under reflux under nitrogen overnight. Then the solvent is evaporated and it is taken up in toluene (25 ml) and is washed twice with water (2×10 ml), then it is dried over sodium sulphate and is evaporated to dryness obtaining the product in the form of a white solid (4.05 g, 94% yield) that does not require further purification.

$^1$H NMR (300 MHz, CDCl$_3$, 298K) δ 6.80-6.73 (m, 3H), 4.11 (t, J=6.4 Hz, 2H), 3.84 (s, 3H), 3.58 (t, J=6.1 Hz, 2H), 3.21 & 3.09 (2×dd, J=10.0, 4.9 Hz, 2×1H), 2.77 (dd, J=13.8, 4.9 Hz, 1H), 2.35 (dd, J=13.8, 9.5 Hz, 1H), 2.10 (quint., J=6.1, 2H), 1.72 (sext., J=6.7, 1H), 1.91-1.10 (m, 1H), 1.01 & 0.95 (2×d, J=6.7, 2×3H)

EXAMPLE 5

Preparation of (S)-4-benzyl-3-(3-methylbutanoyl)oxazolidin-2-one, Compound (XV)

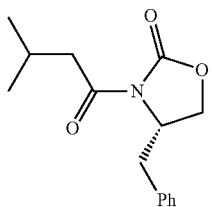 [SMILES: CC(C)CC(=O)N1C(=O)OC[C@@H]1Cc1ccccc1]

4-Dimethylaminopyridine (2.55 g, 21.3 mmol) and triethylamine (46.9 ml, 340.8 mmol) in dichloromethane (100 ml) are added to a solution of (S)-(−)-4-benzyl-2-oxazolidinone (37.7 g, 213 mmol) in dichloromethane (300 ml). Next, isovaleroyl chloride (33.75 ml, 207 mmol) in dichloromethane (50 ml) is added to the previously prepared mixture and cooled to 0° C. keeping the internal temperature below 10° C. The reaction mixture is stirred for 30 minutes at 10° C., then the formed salts are filtered. Water (100 ml) is added and the phases are separated. The organic phase is washed with water (100 ml) and brine (100 ml), dried over sodium sulphate and evaporated to dryness obtaining 53 g of a yellow oil, which solidifies over time (yield 95%).

$^1$H NMR (300 MHz, CDCl$_3$, 298K) δ 7.35-7.15 (m, 5H), 4.71-4.61 (m, 1H), 4.21-4.10 (m, 2H), 3.35-3.25 (dd, J=13.2, J=3.4 Hz, 1H), 2.85-2.72 (dd, J=14.97 Hz, 6.8 Hz, 1H), 2.80-2.67 (m, 2H), 2.29-2.12 (sept, J=13.2 Hz, 1H), 1.03-0.98 (d, J=6.8 Hz, 3H), 0.98-0.95 (d, J=6.8 Hz, 3H).

$^{13}$C NMR (75 MHz, CDCl$_3$, 298K) δ 175.6, 171.2, 154.4, 137.1, 130.5, 130.2, 126.0, 82.1, 66.1, 45.6, 42.6, 41.4, 34.0, 28.7, 27.3, 19.7.

EXAMPLE 6

Preparation of (S)-tert-butyl-3-((S)-4-benzyloxazolidin-2-on-3-yl)-carbonyl-4-methyl-pentanoate, Compound (XVI) in which Z=tert-butyl

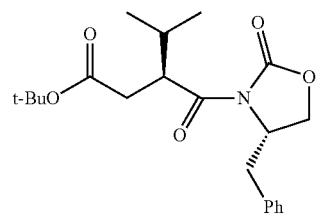 [SMILES: CC(C)[C@H](CC(=O)OC(C)(C)C)C(=O)N1C(=O)OC[C@@H]1Cc1ccccc1]

A solution of hexyllithium 2.3 M in hexane (18.3 ml, 42.1 mmol) is added at 0° C. and under nitrogen to a solution of diisopropylamine (5.19 ml, 42.1 mmol) in anhydrous tetrahydrofuran (10 ml). After 15 minutes the solution is cooled to −78° C. and a solution of (S)-4-benzyl-3-(3-methylbutanoyl)oxazolidin-2-one (compound (XV), 10 g, 38.3 mmol), in THF (5 ml) is added dropwise. After 45 minutes at −78° C., tert-butylbromoacetate (10.7 ml, 72.7 mmol) is added. The temperature is raised to 20° C. in 4 hours, then a saturated solution of ammonium chloride (50 ml) is added, the tetrahydrofuran is evaporated and the suspension thus obtained is extracted twice with ethyl acetate (2×100 ml). The combined organic phases are washed with 0.5N HCl, brine and are dried over sodium sulphate. After evaporating the solvent in a rotary evaporator, 16.48 g of raw product are obtained (orange-coloured solid), which is purified by flash chromatography (8:2 cyclohexane/ethyl acetate), obtaining 6.1 g of product as white solid (yield 50%). Alternatively the product can be purified by crystallizing the raw reaction product from isopropanol.

$^1$H NMR (300 MHz, CDCl$_3$, 298K) δ 7.37-7.20 (m, 5H), 4.70-4.60 (m, 1H), 4.20-4.08 (m, 3H), 3.35-3.25 (dd, J=13.5 Hz, 3.1 Hz, 1H), 2.85-2.75 (dd, J=28.9, 10.1 Hz, 1H), 2.75-2.65 (dd, J=13.8, 10.11 Hz, 1H), 2.47-2.37 (dd, J=16.8 Hz, 3.1 Hz, 1H), 2.01-1.91 (m, 1H), 1.45-1.35 (s, 9H).1.05-0.95 (d, J=6.7 Hz, 3H), 0.95-0.85 (d, J=6.7 Hz, 3H).

$^{13}$C NMR (75 MHz, CDCl$_3$, 298K) δ 176.8, 173.1, 154.4, 137.1, 130.5, 130.2, 178.3, 81.6, 66.9, 57.0, 45.4, 38.5, 34.6, 31.1, 29.2, 21.7, 19.5.

EXAMPLE 7

Preparation of (S)-benzyl-3-((S)-4-benzyloxazolidin-2-on-3-yl)-carbonyl-4-methyl-pentanoate, Compound (XVI) in which Z=benzyl

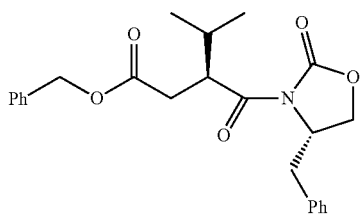 [SMILES: CC(C)[C@H](CC(=O)OCc1ccccc1)C(=O)N1C(=O)OC[C@@H]1Cc1ccccc1]

The product is obtained as in the procedure described in the preceding example and using benzyl bromoacetate instead of tert-butylbromoacetate. The product is obtained by crystallization from isopropanol (yield 72%) as a white solid, m.p. 104° C.

$^1$H NMR (300 MHz, CDCl$_3$, 298K) δ 7.34-7.23 (m, 10H), 5.10 (s, 2H), 4.63-4.59 (m, 1H), 4.27-4.21 (m, 1H), 4.12-4.08 (m, 2H), 3.22 (dd, J=13.5, 3.1 Hz, 1H), 3.03 (dd, J=17.2, 11.9 Hz), 2.58 (dd, J=9.5, 6.4 Hz, 1H), 2.47 (dd, J=13.5, 10.1 Hz, 1H), 2.07-1.97 (m, 1H), 1.02 (d, J=6.7 Hz, 3H), 0.92 (d, J=6.7 Hz, 3H).

$^{13}$C NMR (75 MHz, CDCl$_3$, 298K) δ 176.6, 173.7, 137.3, 130.9, 130.3, 1230.0, 129.7, 129.6, 128.5, 68.0, 67.2, 57.1, 45.7, 38.6, 33.8, 31.3, 22.1, 19.7.

EXAMPLE 8

Preparation of (S)-3-((S)-4-benzyloxazolidin-2-on-3-yl)-carbonyl-4-methyl pentanoic acid, Compound (XVI') (from Deprotection of the Corresponding tert-butyl ester)

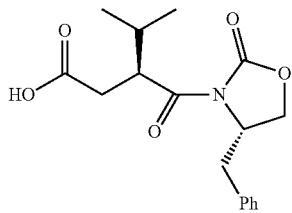

(S)-Tert-butyl-3-((S)-4-benzyloxazolidin-2-on-3-yl)-carbonyl-4-methyl pentanoate (3.17 g, 8.4 mmol) is dissolved in 95 ml of a 1:2 v/v solution of trifluoroacetic acid and dichloromethane and the mixture is stirred at room temperature overnight. It is evaporated to residue under vacuum obtaining 2.03 g of an oil, which is purified by flash chromatography, eluting with 1:1 cyclohexane/ethyl acetate to give 1.75 g of product as a white solid (yield 65%), which shows 2 endothermic effects at 122.5° C. and 209.2° C. in DSC.

$^1$H NMR (300 MHz, CDCl$_3$, 298K) δ 7.35-7.20 (m, 5H), 4.61-4.59 (m, 1H), 4.2-4.10 (m, 3H), 3.29-3.19 (dd, J=13.5 Hz, 3.1 Hz, 1H), 3.03-2.89 (dd, J=17.8, 11.6 Hz, 1H), 2.75-2.65 (dd, J=13.5, 9.5 Hz, 1H), 2.57-2.47 (dd, J=17.9, 3.1 Hz, 1H), 2.03-1.93 (m, 1H), 1.01-0.91 (d, J=6.75 Hz, 3H), 0.91-0.81 (d, J=6.75 Hz, 3H).

$^{13}$C NMR (75 MHz, CDCl$_3$, 298K) δ 180.3, 176.3, 154.4, 136.8, 130.9, 130.2, 128.5, 67.1, 56.9, 45.3, 38.4, 32.9, 31.0, 22.0, 19.3.

EXAMPLE 9

Preparation of (S)-3-((S)-4-benzyloxazolidin-2-on-3-yl)-carbonyl-4-methyl pentanoic acid, Compound (XVI') (from Hydrogenolysis of the Corresponding benzyl ester)

The hydrogenolysis of (S)-benzyl-3-((S)-4-benzyloxazolidin-2-on-3-yl)-carbonyl-4-methyl pentanoate (100 g, 244 mmol) in THF (600 ml) is carried out with 10% Pd/C (2 mol. %) and hydrogen at atmospheric pressure (rubber flask) for 24 hours. After filtration of the catalyst and concentration to residue under vacuum, the oil thus obtained is treated with heptane, obtaining the product (74.0 g, yield 95%) in the form of a colourless solid.

EXAMPLE 10

Preparation of (S)-ethyl-5-(((S)-4-benzyloxazolidin-2-on-3-yl)carbonyl)-6-methyl-3-oxoheptanoate, Compound (III) in which R is ethyl and Y is the Radical (S)-4-benzyloxazolidin-2-on-3-yl

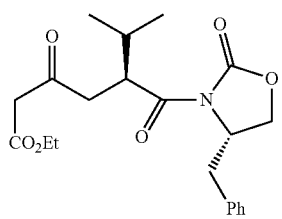 [SMILES: CCOC(=O)CC(=O)C[C@H](C(=O)N1C(=O)OC[C@@H]1Cc1ccccc1)C(C)C]

A 100-ml flask is charged with potassium ethyl-malonate (7.99 g, 46.9 mmol), anhydrous THF (20 ml) and anhydrous magnesium chloride (2.24 g, 23.5 mmol). The suspension is heated under reflux under nitrogen for 12 hours, then it is cooled to 20-22° C. A solution prepared by addition, under nitrogen and at 0° C., of carbonyl diimidazole (2.79 g, 17.2 mmol) to (S)-3-((S)-4-benzyloxazolidin-2-on-3-yl)-carbonyl-4-methyl pentanoic acid (5.0 g, 15.65 mmol) in anhydrous THF (15 ml) and then heating at 20° C. for 2 hours, is added to this suspension. The resultant mixture is stirred at 20-22° C. for 3 hours, then 10% w/w aqueous solution of HCl (about 80 ml) is added to pH=2. The tetrahydrofuran is evaporated at reduced pressure and the mixture is extracted with toluene (80 ml); the organic phase is washed twice with a saturated solution of NaHCO$_3$ (80 ml), dried over sodium sulphate and concentrated to residue. The product is obtained in the form of a viscous oil that does not require further purification (5.5 g, yield 90%).

$^1$H NMR (300 MHz, CDCl$_3$, 298K) δ 7.30-7.10 (m, 5H), 4.62-4.52 (m, 1H), 4.15-4.00 (m, 5H), 3.48-3.32 (q, J=13.20 Hz, 2H), 3.22-3.12 (dd, J=13.2, 2.8 Hz, 1H), 3.12-2.02 (dd, J=18.4, 11.6 Hz, 1H), 2.75-2.65 (dd, J=14.0, 2.8 Hz, 1H), 1.97-1.87 (m, 1H), 1.22-1.15 (t, J=6.7 Hz, 3H), 0.95-0.90 (d, J=6.7 Hz, 3H), 0.83-0.78 (d, J=6.7 Hz, 3H).

$^{13}$C NMR (75 MHz, CDCl$_3$, 298K) δ 202.9, 176.5, 168.3, 154.5, 137.2, 130.3, 130.2, 128.5, 67.1, 63.0, 57.0, 50.6, 44.8, 42.7, 38.7, 30.9, 22.0, 21.2, 15.4

EXAMPLE 11

Preparation of (S)-1-benzyl-4-tert-butyl-2-isopropyl-succinate, Compound (XVII) in which R is tert-butyl

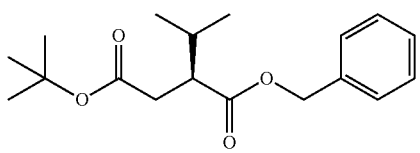 [SMILES: CC(C)[C@H](CC(=O)OC(C)(C)C)C(=O)OCc1ccccc1]

A 2500-ml two-necked flask is charged under nitrogen with (S)-tert-butyl-3-((S)-4-benzyloxazolidin-2-on-3-yl)-carbonyl-4-methyl pentanoate (25.0 g, 66.6 mmol), anhydrous tetrahydrofuran (100 ml) is added and it is cooled to 0° C. A solution prepared by dissolving benzyl alcohol (9.36 g, 86.6 mmol) in anhydrous tetrahydrofuran (25 ml), cooling to −10° C. and adding dropwise a 2.3 M solution of hexyllithium in hexane (31.8 ml, 73.2 mmol), is added to this solution at 0° C. It is kept at 0° C. for 6 hours, monitoring the reaction by HPLC, then water (250 ml) and 150 ml of ethyl acetate are added. The phases are separated, the organic phase is washed with water (100 ml) and the organic phase is concentrated to residue, obtaining 36 g of raw product. The raw product is taken up in ethyl acetate (40 ml) and hexane (200 ml); it is stirred for 30 minutes and the precipitated Evans auxiliary is filtered. The filtrate is concentrated to residue and is purified by flash chromatography (hexane-ethyl acetate 7:3, $R_f$ product=0.7; $R_f$ starting=0.6) obtaining the product in the form of colourless oil (16 g, yield 79%).

$^1$H NMR (300 MHz, CDCl$_3$, 298K) δ 7.4-7.2 (m, 5H), 5.09 & 5.14 (system AB, J=11.0 Hz, 2×1H), 2.79-2.60 (m, 2H), 2.38-2.28 (m, 1H), 1.97 (sext. J=5.5 Hz, 1H), 1.40 (s, 9H), 0.90 & 0.87 (2×d, J=7.4 Hz, 2×3H).

EXAMPLE 12

Preparation of (S)-3-(benzyloxycarbonyl)-4-methylpentanoic acid, Compound (XIX)

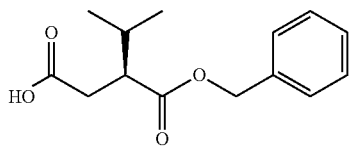 [SMILES: CC(C)[C@H](CC(=O)O)C(=O)OCc1ccccc1]

A 250-ml flask is charged with (S)-1-benzyl-4-tert-butyl-2-isopropylsuccinate (20 g, 65.3 mmol), trifluoroacetic acid (80 ml) and is stirred under nitrogen at room temperature for 2 hours, monitoring the reaction by TLC (hexane-ethyl acetate 7:3, molybdic development, acid $R_f$=0.4, tert-butyl ester $R_f$=0.8). The trifluoroacetic acid is distilled at ambient pressure with the purpose of recovering it, the last traces of acid are removed under vacuum and the residue is taken up in toluene (100 ml) and saturated aqueous solution of NaHCO$_3$ (600 ml); the desired product is extracted in the aqueous phase. The aqueous phase is washed with toluene (100 ml) and the product is extracted in toluene after adjusting the pH to 2 with 1M H$_2$SO$_4$. The toluene is concentrated to residue, then it is taken up in methyl tert-butyl ether (200 ml) and cyclohexylamine is added until there is quantitative precipitation of the product and it is filtered. The product is washed with methyl tert-butyl ether and is dried under vacuum at 25° C. The cyclohexylammonium salt of the desired product is suspended in toluene and is acidified with 1N HCl to pH=2, the phases are separated and the organic phase is concentrated to residue, obtaining the desired product in the form of pale yellow oil (13.8 g, yield 85%).

$^1$H NMR (300 MHz, CDCl$_3$, 298K) δ 11.4 (bs, 1H), 7.35-7.25 (m, 5H), 5.15 (s, 2H), 2.86-2.75 (m, 2H), 2.52-2.40 (m, 1H), 0.98 & 0.90 (2×d, J=7.4 Hz, 2×3H).

EXAMPLE 13

Preparation of (S)-1-benzyl-6-ethyl-2-isopropyl-4-oxohexanedioate, Compound (III) in which R is ethyl and Y is —OR, with R benzyl

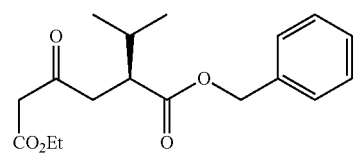 [SMILES: CCOC(=O)CC(=O)C[C@H](C(=O)OCc1ccccc1)C(C)C]

The product is obtained by a procedure similar to that described in example 10 using (S)-3-(benzyloxycarbonyl)-4-methylpentanoic acid instead of (S)-3-((S)-4-benzyloxazolidin-2-on-3-yl)-carbonyl-4-methyl pentanoic acid. Yield isolated after flash chromatography 72%.

$^1$H NMR (300 MHz, CDCl$_3$, 298K) δ 7.40-7.20 (m, 5H), 5.12 & 5.05 (system AB, J=12.2 Hz, 2×1H), 4.15 (q, J=7.0, 2H), 3.48 & 3.38 (system AB, J=15.3 Hz, 2×1H), 3.03-2.85 (m, 2H), 2.59 (dd, J=17.4, 3.0, 1H), 2.05 (sext. J=5.2, 1H), 1.24 (t, J=7.0, 3H), 0.88 & 0.85 (2×d, J=7.4 Hz, 2×3H).

EXAMPLE 14

Preparation of (S)-dibenzyl-2-isopropyl-4-oxohexanedioate, Compound (III) in which R is benzyl and Y is —OR, with R benzyl

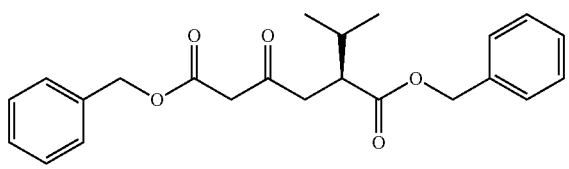 [SMILES: CC(C)[C@H](CC(=O)CC(=O)OCc1ccccc1)C(=O)OCc1ccccc1]

The product is obtained by a procedure similar to that described in example 10 using (S)-3-(benzyloxycarbonyl)-4-methylpentanoic acid instead of (S)-3-((S)-4-benzyloxazolidin-2-on-3-yl)-carbonyl-4-methyl pentanoic acid and the potassium salt of monobenzyl malonic acid instead of the potassium salt of monoethyl malonic acid. Yield isolated after flash chromatography 69%.

$^1$H NMR (300 MHz, CDCl$_3$, 298K) δ 7.34-7.25 (m, 10H), 5.16 (s, 2H), 5.12 & 5.06 (system AB, J=12.5, 2×1H), 3.54 & 3.45 (system AB, J=15.3 Hz, 2×1H), 3.02-2.82 (m, 2H), 2.55 (dd, J=17.4, 3.0, 2×1H), 2.05-1.92 (m.1H), 0.86 & 0.83 (2×d, J=10.4, 2×3H).

EXAMPLE 15

Preparation of (S)-1-benzyl-6-tert-butyl-2-isopropyl-4-oxohexanedioate, Compound (III) in which R is tert-butyl and Y is —OR, with R benzyl

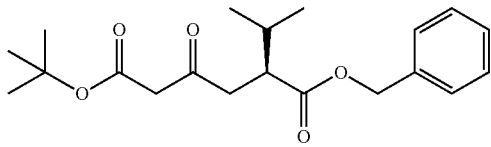 [SMILES: CC(C)[C@H](CC(=O)CC(=O)OC(C)(C)C)C(=O)OCc1ccccc1]

The product is obtained by a procedure similar to that described in example 10 using (S)-3-(benzyloxycarbonyl)-4-methylpentanoic acid instead of (S)-3-((S)-4-benzyloxazolidin-2-on-3-yl)-carbonyl-4-methyl pentanoic acid and the potassium salt of monotert-butyl malonic acid instead of the potassium salt of monoethyl malonic acid. Yield isolated after flash chromatography 82%.

$^1$H NMR (300 MHz, CDCl$_3$, 298K) δ 7.40-7.30 (m, 5H), 5.06 & 5.00 (system AB, J=12.4 Hz, 2×1H), 3.32 & 3.22 (system AB, J=15.1 Hz, 2×1H), 2.91 (dd, J=17.6, 10.4 Hz, 1H), 2.79 (ddd, J=10.4, 5.2, 3.3 Hz, 1H), 2.53 (dd, J=17.6, 3.3 Hz, 1H), 1.94 (d sept, J=6.7, 1.6 Hz, 1H), 1.38 (s, 9H), 0.84 & 0.79 (2×d, J=6.7 Hz, 2×3H).

$^{13}$C NMR (75 MHz, CDCl$_3$, 298K) δ 201.9, 174.2, 166.3, 136.1, 128.5, 128.3, 128.2, 82.0, 66.4, 50.9, 46.2, 41.0, 30.0, 28.0, 20.2, 19.5.

EXAMPLE 16

Preparation of (S)-ethyl-5-(((S)-4-benzyloxazolidin-2-on-3-yl)carbonyl)-2-((R)-2-(4-methoxy-3-(3-methoxypropoxy)benzyl)-3-methylbutylidene)-6-methyl-3-oxoheptanoate (E/Z Mixture), Compound (IV) in which R is ethyl and Y is the Radical (S)-4-benzyloxazolidin-2-on-3-yl

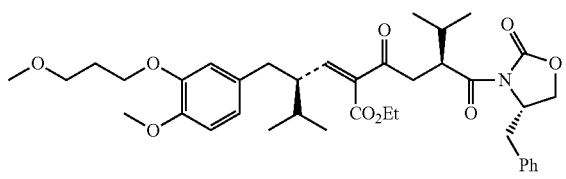

A four-necked flask is charged under nitrogen with anhydrous tetrahydrofuran (200 ml); it is cooled to 0° C. and a solution of titanium tetrachloride (18.40 g, 0.097 mol) in dichloromethane (24 ml) is added. A pale yellow suspension forms. A solution, prepared by dissolving the aldehyde obtained in example 4A (14.3 g, 0.0485 mol), the beta-ketoester prepared in example 10 (18.89 g, 0.0485 mol) in tetrahydrofuran (67 ml), is added at 0° C.

A solution of pyridine (15.35 g, 0.194 mol) in tetrahydrofuran (26 ml) is added to the resultant solution, at 0° C. in 2 hours. It is reacted for 14 hours, allowing the temperature to rise to 15° C. Then it is cooled again to 0° C. and water (150 ml) and methyl-tert-butyl ether (200 ml) are added. The phases are separated, the aqueous phase is extracted with methyl-tert-butyl ether (150 ml), the combined organic phases are washed with brine (200 ml), dried over sodium sulphate and concentrated to residue. The resultant orange-coloured oil is purified by flash chromatography with gradient elution hexane-ethyl acetate 100:0→70:30 obtaining the desired product in the form of an approx. 1:3 mixture by HPLC of isomers of the double bond (yellow oil, 15.0 g, yield 46%).

ESI MS: m/z 688.2 (M+Na).

EXAMPLE 17

Preparation of (5S)-ethyl-5-(((S)-4-benzyloxazolidin-2-on-3-yl)carbonyl)-2-((R)-2-(4-methoxy-3-(3-methoxypropoxy)benzyl)-3-methylbutyl)-6-methyl-3- oxoheptanoate, Compound (V) in which R is ethyl and Y is the Radical (S)-4-benzyloxazolidin-2-on-3-yl

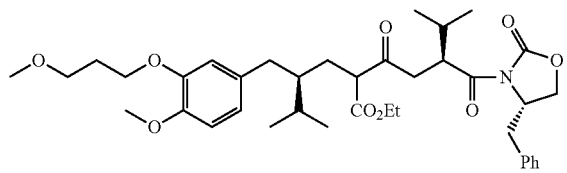 [SMILES: CCOC(=O)C(C[C@H](Cc1ccc(OC)c(OCCCOC)c1)C(C)C)C(=O)C[C@H](C(=O)N1C(=O)OC[C@@H]1Cc1ccccc1)C(C)C]

The product obtained in example 16 (13.5 g, 0.0207 mol) is hydrogenated in tetrahydrofuran (70 ml) with 10% Pd/C (water content 55%, 601 mg, 0.31 mmol) with hydrogen at atmospheric pressure (rubber balloon) until the starting product has disappeared (which takes about 24 hours). Then the catalyst is filtered and evaporation to dryness gives the product in the form of colourless oil (13.5 g, yield 100%).

ESI MS: m/z 690.2 (M+Na)

EXAMPLE 18

Preparation of (S,E)-ethyl-3-acetoxy-5-(((S)-4-benzyloxazolidin-2-on-3-yl)carbonyl)-2-((S)-2-(4-methoxy-3-(3-methoxypropoxy)benzyl)-3-methylbutyl)-6-methylhept-2-enoate, Compound (VI) in which R is ethyl, Y is the Radical (S)-4-benzyloxazolidin-2-on-3-yl and P is acetyl

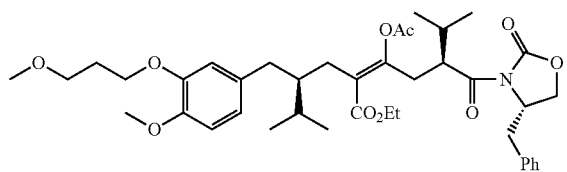 [SMILES: CCOC(=O)/C(C[C@H](Cc1ccc(OC)c(OCCCOC)c1)C(C)C)=C(\C[C@H](C(=O)N1C(=O)OC[C@@H]1Cc1ccccc1)C(C)C)OC(C)=O]

The beta-ketoester obtained as described in example 17 (3.91 g, 5.86 mmol) is dissolved under nitrogen in acetic anhydride (46 ml), and 4-dimethylaminopyridine (358 mg, 2.93 mmol) and triethylamine (6.52 ml, 46.9 mmol) are added. The reaction is monitored by HPLC; after 3 hours the reaction is completed and the mass is evaporated to residue. Then it is taken up in toluene and is washed with water to neutral pH. The residue is purified by flash chromatography with gradient elution hexane-ethyl acetate 100:0→70:30, obtaining the desired product (3.45 g, yield 83%) as colourless oil.

ESI MS: m/z 732.3 (M+Na)

$^1$H NMR (300 MHz, CDCl$_3$, 298K) δ 7.45-7.25 (m, 4H), 7.15-7.17 (m, 1H), 6.65-6.85 (m, 3H), 4.51-4.62 (m, 1H), 4.20-4.05 (m, 5H), 4.03 (t, J=6.4 Hz, 2H), 3.75 (s, 3H), 3.53 (t, J=6.1 Hz, 3H), 3.33 (s, 3H), 3.29-3.17 (m, 1H), 2.94 (dd, J=15.0, 4.0 Hz, 1H), 2.62-2.54 (m, 1H), 2.41-2.35 (m, 1H), 2.25-1.85 (m, 7H), 1.70-1.50 (m, 1H), 1.58 (s, 3H), 1.20 (t, J=7.0 Hz, 3H), 0.96 & 0.94 & 0.85 & 0.80 (4×d, J=10.0 Hz, 4×3H).

$^{13}$C NMR (75 MHz, CDCl$_3$, 298K) δ 174.9, 168.4, 167.7, 155.8, 153.3, 148.3, 147.6, 135.8, 134.3, 129.6, 129.4, 127.3, 124.4, 121.4, 114.6, 111.9, 69.5, 66.2, 65.8, 60.8, 58.7, 56.2, 55.7, 46.0, 45.6, 37.8, 36.0, 31.3, 30.3, 29.7, 28.2, 27.7, 20.5, 18.7, 18.6, 18.5, 18.4, 14.3.

EXAMPLE 19

Preparation of (5S)-6-benzyl-1-ethyl-5-isopropyl-2-((R)-2-(4-methoxy-3-(3-methoxypropoxy)benzyl)-3-methylbutyl)-3-oxohexanedioate, Compound (V) in which R is ethyl and Y is —OR with R benzyl chromatography with gradient elution hexane-ethyl acetate 100:0→70:30, obtaining the desired product (597 mg, yield 71%).

$^1$H NMR (300 MHz, CDCl$_3$, 298K) δ 7.33-7.25 (m, 5H), 6.76-6.62 (m, 3H), 5.13-5.02 (m, 2H), 4.12 (q, J=7.1 Hz, 2H), 4.07 (t, J=6.4 Hz, 2H), 3.80 (s, 3H), 3.54 (t, J=6.4 Hz, 2H), 3.47-3.31 (m, 1H), 3.32 (s, 3H), 3.01-2.71 (m, 2H), 2.58-2.44 (m, 1H), 2.41-2.25 (m, 2H), 2.07 (sext., J=6.4 Hz, 2H), 1.98-1.84 (m, 2H), 1.76-1.52 (m, 2H), 1.50-1.36 (m, 1H), 1.22 & 1.16 (2×t, J=7.1 Hz, mixture≈1:1 of diastereoisomers, 3H), 0.92-0.79 (m, 12H).

$^{13}$C NMR (75 MHz, CDCl$_3$, 298K) δ 205.7 (diast. 1), 205.5 (diast. 2), 175.9 (diast. 1), 175.4 (diast. 2), 171.6 (diast. 1), 171.4 (diast. 2), 150.2, 149.5, 137.8, 135.8 (diast. 1), 135.6 (diast. 2), 130.24, 130.20, 129.94, 129.87, 129.80, 123.0 (diast. 1), 122.9 (diast. 2), 116.1, 113.6, 71.1, 68.04 (diast. 1), 67.97 (diast. 2), 67.9, 63.07 (diast. 1), 62.99 (diast. 2), 60.4, 59.6 (diast. 1), 59.2 (diast. 2), 57.8, 47.8 (diast. 1), 47.7 (diast. 2), 45.3 (diast. 1), 45.0 (diast. 2), 41.9 (diast. 1), 41.6 (diast. 2), 38.7 (diast. 1), 38.3 (diast. 2), 31.7 (diast. 1), 31.6 (diast. 2), 31.4, 31.1 (diast. 1), 31.0 (diast. 2), 30.6, [21.82, 21.79, 21.4, 21.3, 20.9, 20.4, 20.3, 19.7 (diast. 1 and 2)], 15.9 (diast. 1), 15.8 (diast. 2).

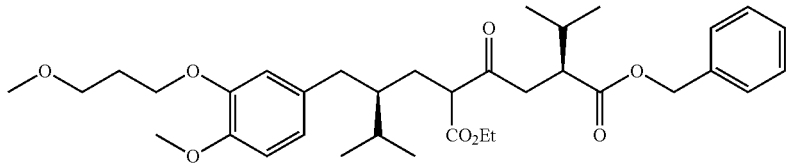 [SMILES: CCOC(=O)C(C[C@H](Cc1ccc(OC)c(OCCCOC)c1)C(C)C)C(=O)C[C@H](C(=O)OCc1ccccc1)C(C)C]

A 25-mL flask is charged under nitrogen with the iodide obtained in example 4B (593 mg, 1.475 mmol) and the beta-ketoester obtained in example 12 (450 mg, 1.404 mmol), they are dissolved in anhydrous dimethylacetamide (7 ml) and potassium carbonate is added as fine powder (213.5 mg, 1.515 mmol). It is stirred under nitrogen for 24 hours at 25° C., monitoring by TLC (eluent ethyl acetate-hexane 3:7, R$_f$ iodide=0.42, R$_f$ beta-ketoester=0.37, R$_f$ product=0.31).

Then it is diluted with ethyl acetate (30 ml) and is washed with water until the dimethylacetamide has been removed completely. After drying the organic phase over sodium sulphate it is evaporated to dryness and is purified by flash

EXAMPLE 19A

Preparation of (5S)-6-benzyl-1-tert-butyl-5-isopropyl-2-((R)-2-(4-methoxy-3-(3-methoxypropoxy) benzyl)-3-methylbutyl)-3-oxohexanedioate, Compound (V) in which R is tert-butyl and Y is —OR with R=benzyl

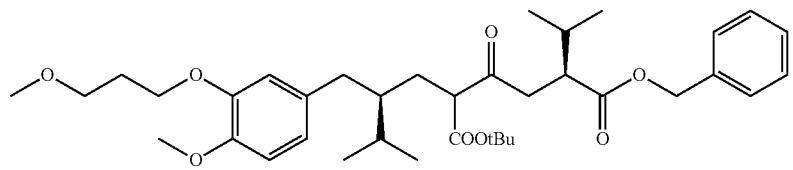

A 500-mL flask is charged under nitrogen with the iodide obtained in example 4B (45.34 g, 0.112 mol) and the beta-ketoester obtained in example 15 (37.0 g, 0.116 mol), they are dissolved in anhydrous dimethylacetamide (150 ml) and potassium carbonate is added as fine powder (16.16 mg, 0.117 mol). It is stirred under nitrogen for 24 hours at 25° C., monitoring by TLC (eluent ethyl acetate-hexane 3:7, $R_f$ iodide=0.42, $R_f$ beta-ketoester=0.37, $R_f$ product=0.31) or by HPLC.

Then it is cooled to 0° C., it is diluted with ethyl acetate (300 ml) and is washed with water until the dimethylacetamide is removed completely. After drying the organic phase over sodium sulphate it is evaporated to dryness and is purified by flash chromatography with gradient elution hexane-ethyl acetate 100:0→70:30, obtaining the desired product (pure fractions 18 g, 50%).

$^1$H NMR (300 MHz, CDCl$_3$, 298K) δ 7.34-7.25 (m, 5H), 6.77-6.56 (m, 3H), 5.14 & 5.07 (system AB, J=13.2 Hz, 2×1H), 4.08 (t, J=5.2 Hz, 2H), 3.82 (s, 3H), 3.56 (t, J=4.9 Hz, 2H), 3.34 (s, 3H), 3.35-3.32 (m, 1H), 3.04-2.71 (m, 2H), 2.58-2.27 (m, 3H), 2.09 (doubled quintuplet, J=6.4, 2.5 Hz, 2H), 2.01-1.81 (m, 2H), 1.77-1.62 (m, 2H), 1.60-1.40 (m, 2H), 1.44 (s, 6H), 1.37 (s, 3H), 0.94-0.78 (m, 12H).

EXAMPLE 20

Preparation of (S,E)-6-benzyl-1-tert-butyl-3-acetoxy-5-isopropyl-2-((S)-2-(4-methoxy-3-(3-methoxypropoxy)benzyl)-3-methylbutyl)hex-2-enedioate, Compound (VI) in which R is tert-butyl, Y is OR where R is benzyl and P is acetyl

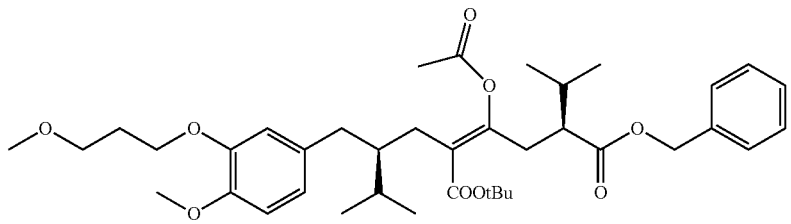

The beta-ketoester obtained as described in example 19A (3.71 g, 5.92 mmol) is dissolved under nitrogen in acetic anhydride (12 ml), and 4-dimethylaminopyridine (361 mg, 2.96 mmol) and triethylamine (6.60 ml, 47.35 mmol) are added. The reaction is monitored by HPLC; after 3 hours the reaction is completed and the mass is evaporated to residue. Then it is taken up in toluene and is washed with a saturated water solution of sodium bicarbonate, water and finally brine. The residue is purified by flash chromatography with gradient elution hexane-ethyl acetate 100:0→70:30, obtaining the desired product (3.16 g, yield 80%) as colourless oil.

$^1$H NMR (300 MHz, CDCl$_3$, 298K) δ 7.33-7.30 (m, 5H) 6.76-6.63 (m, 3H), 5.11 & 5.06 (system AB, J=12.5 Hz, 2×1H), 4.07 (t, J=6.4 Hz, 2H), 3.81 (s, 3H), 3.56 (t, J=6.1 Hz, 2H), 3.34 (s, 3H), 2.98 (dd, J=14.7, 4.5 Hz, 1H), 2.81 (dd, 14.7, 10.1 Hz, 1H), 2.46-2.38 (m, 2H), 2.28-2.18 (m, 1H), 2.15-2.10 (m, 4H), 1.96 (s, 3H), 1.92-1.82 (m, 1H), 1.72-1.64 (m, 1H), 1.55 (s, 9H), 1.45-1.40 (m, 1H), 0.94 & 0.88 & 0.87 & 0.80 (4×d, J=6.7 Hz, 4×3H).

EXAMPLE 21

Preparation of (S,E)-3-acetoxy-5-(benzyloxycarbonyl)-2-((S)-2-(4-methoxy-3-(3-methoxypropoxy)benzyl)-3-methylbutyl)-6-methylhept-2-enoic acid, Compound (VI) in which R is H, Y is OR where R is benzyl and P is acetyl

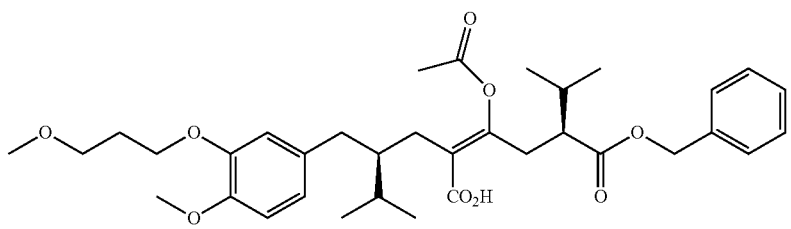 [SMILES: COCCCOc1cc(C[C@@H](C/C(C(=O)O)=C(/C[C@H](C(=O)OCc2ccccc2)C(C)C)OC(C)=O)C(C)C)ccc1OC]

In a 50-mL flask under nitrogen and with magnetic stirring, the enol acetate tert-butylester obtained in example 18 (8.20 g, 12.26 mmol) is dissolved in trifluoroacetic acid (25 mL) and is stirred at room temperature for 1 hour. The trifluoroacetic acid is evaporated and the last traces thereof are removed by evaporation with toluene under vacuum. 7.5 g of the desired product are obtained as yellow oil (quantitative yield).

$^1$H NMR (300 MHz, CDCl$_3$, 298K) δ 7.33-7.31 (m, 5H), 6.76-6.60 (m, 3H), 5.13 & 5.04 (system AB, J=12.3H, 2×1H), 4.21-4.08 (m, 2H), 3.82 (s, 3H), 3.60 (t, J=6.1 Hz, 2H), 3.39 (s, 3H), 2.99 (dd, J=14.4, 3.7 Hz, 1H), 2.78 (dd, J=14.4, 11.0, 1H), 2.58-2.42 (m, 2H), 2.27-2.10 (m, 2H), 2.00 (s, 3H), 1.91 (sext., J=6.7 Hz, 1H), 1.73-1.64 (m, 1H), 0.93-0.79 (m, 12H).

$^{13}$C NMR (75 MHz, CDCl$_3$, 298K) δ 175.2, 171.1, 168.2, 158.2, 148.1, 147.8, 135.9, 134.2, 128.6, 128.3, 128.2, 123.9, 121.7, 115.0, 112.0, 69.5, 66.4, 66.2, 58.6, 56.1, 50.9, 45.3, 35.8, 32.0, 31.2, 29.4, 28.3, 28.2, 20.6, 20.1, 20.0, 18.9, 18.5.

EXAMPLE 22

Preparation of (2S,3S,5S)-3-acetoxy-5-(benzyloxycarbonyl)-2-((R)-2-(4-methoxy-3-(3-methoxypropoxy)benzyl)-3-methylbutyl)-6-methylheptanoic acid, Compound (VI) in which R is H, Y is OR where R is benzyl and P is acetyl

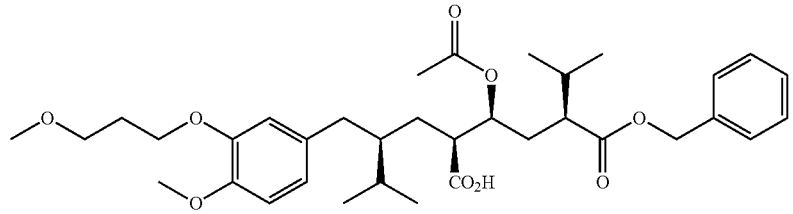 [SMILES: COCCCOc1cc(C[C@@H](C[C@H](C(=O)O)[C@H](C[C@H](C(=O)OCc2ccccc2)C(C)C)OC(C)=O)C(C)C)ccc1OC]

A 50-mL steel autoclave inertized with nitrogen is charged with [((S)-PhanePhos)Rh(cod)]BF$_4$ (87 mg, 0.1 mmol, 1 mol. %), a solution of the enol acetate acid prepared in example 21 (6.2 g, 10.0 mmol) in ethanol (20 mL) is added, and triethylamine (0.97 mL, 7.0 mmol) is added.

After 3 cycles of vacuum/nitrogen and 3 cycles of vacuum/hydrogen, it is pressurized to 30 bar of hydrogen and is heated at 60° C. for 6 hours.

Then it is cooled, the ethanolic solution is concentrated to residue, it is taken up in methylene chloride (30 mL) and it is washed with 1N HCl (20 mL). The organic phase is separated, it is dried over MgSO$_4$ and it is evaporated to dryness, obtaining the desired product in the form of dark oil in quantitative yield. Chiral HPLC analysis after derivatization with diazomethane (column: Diacel AD-H 0.46×15 cm, eluent: hexane-isopropanol 95:5, T=40° C., λ=205 nm, T$_r$ isomer 1=8.6 min, T$_r$ isomer 2=9.5 min) shows a diastereomeric ratio (d.r.) <1:>99.

The same reaction carried out using [Rh(DiPFc)(cod)]BF$_4$ as catalyst shows a diastereomeric excess (d.r.) of 4:96.

The same reaction carried out using [Ru(R-Binap)(benzene)Cl]Cl as catalyst shows a diastereomeric excess (d.r.) of 3:97.

$^1$H NMR (300 MHz, CDCl$_3$, 298K) δ 7.39-7.28 (m, 5H), 6.75-7.72 (m, 2H), 6.65 (dd, J=9.9, 1.6 Hz, 1H), 5.17 & 5.04 (system AB, J=12.2 Hz, 2×1H), 5.06 (td, J=7.1, 4.1 Hz, 1H), 4.14 (t, J=6.9 Hz, 2H), 3.81 (s, 3H), 3.63-3.54 (m, 2H), 3.36 (s, 3H).2.73-2.63 (m, 1H), 2.53 (dd, J=13.7, 5.5 Hz, 1H), 2.39 (dd, J=13.7, 8.3 Hz, 1H), 2.27-2.15 (m, 1H), 2.15-1.95 (m, 3H), 1.92 (s, 3H), 1.72-1.54 (m, 3H), 1.28-1.15 (m, 1H), 0.87 (d, J=6.6 Hz, 3H), 0.83 (d, J=6.9 Hz, 3H), 0.81 (d, J=6.9 Hz, 6H).

$^{13}$C NMR (75 MHz, CDCl$_3$, 298K) δ 176.4, 174.6, 170.2, 148.3, 147.8, 136.1, 134.1, 128.6, 128.5, 128.2, 121.3, 114.1, 111.6, 72.7, 69.7, 66.5, 66.2, 58.7, 56.2, 53.6, 48.2, 47.8, 44.2, 36.9, 31.1, 29.4, 29.0, 28.7, 20.9, 20.4, 19.9, 17.5.

LC-MS (ESI): m/z 637 (M+Na$^+$)

EXAMPLE 23

Preparation of (2S,4S,5S,7S)-benzyl-4-acetoxy-5-(benzyloxycarbonylamino)-2,7-diisopropyl-8-[4-methoxy-3-(3-methoxypropoxy)phenyl]octanoate, Compound (VI"") in which W is Cbz, Y is OR where R is benzyl and P is acetyl

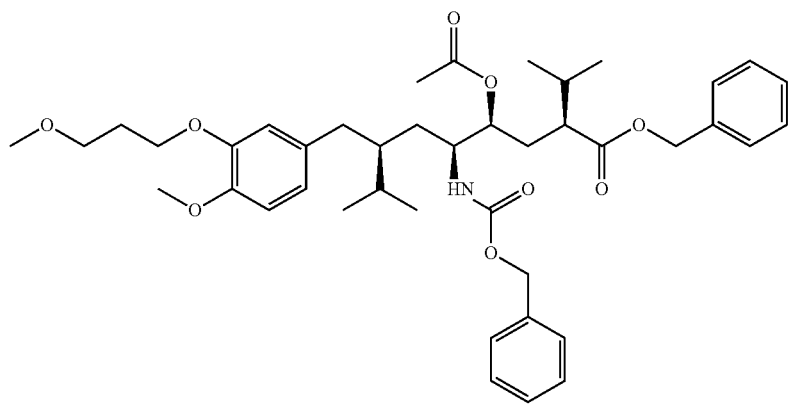 [SMILES: COCCCOc1cc(C[C@@H](C[C@H](NC(=O)OCc2ccccc2)[C@H](C[C@H](C(=O)OCc2ccccc2)C(C)C)OC(C)=O)C(C)C)ccc1OC]

A 500-mL four-necked flask equipped with thermometer, mechanical stirrer, and dropping funnel is charged under a nitrogen stream with the acid obtained in example 22 (21.0 g, 34.2 mmol); the acid is dissolved in 85 mL of acetone, it is cooled to −10° C., triethylamine (3.80 g, 37.6 mmol) is added, it is stirred for 5 minutes and then a solution of ethyl chloroformate (4.1 g, 37.6 mmol) in acetone (28.3 mL) is added dropwise in about 30 minutes without exceeding a temperature of 0° C. It is stirred for 30 minutes; while keeping the internal temperature at −10° C., a solution of sodium azide (4.4 g, 68.3 mmol) in water (13.2 mL) is added. After addition, it is stirred for 1 hour and the course of the reaction is monitored by HPLC. At the end of reaction, the reaction mixture is poured into 200 g of crushed ice and is extracted with toluene (2×200 mL). The toluene phase is heated to 90° C. to convert the acyl azide to isocyanate (evolution of nitrogen is observed), monitoring the reaction by HPLC. On completion of conversion, 250 mL of toluene are distilled, then benzyl alcohol (3.14 g, 29 mmol) and triethylamine (4.15 g, 41.0 mmol) are added and it is heated under reflux for 6 hours. The reaction is monitored by HPLC until the isocyanate disappears.

The reaction mixture is poured into water (100 mL) and the phases are separated hot, the organic phase is washed with 1N HCl (100 mL) and concentrated to residue.

Purification by flash chromatography gives 18.1 g of pure fractions of the desired product (yield 73.5%).

$^1$H NMR (400 MHz, CDCl$_3$, 298K) δ 7.24-7.27 (m, 10H), 6.82-6.74 (m, 2H), 6.71-6.64 (m, 1H), 5.22-5.03 (m, 4H), 4.89 (td, J=10.2, 3.3 Hz, 1H), 4.72 (d, J=11.5 Hz, 1H), 4.20-4.08 (m, 2H), 3.91-3.80 (m.1H), 3.84 (s, 3H), 3.59 (1H, t, J=6.28 Hz), 3.34 (s, 3H), 2.50 (ddd, J=21.8, 13.5, 7.3 Hz, 1H), 2.27-2.20 (m, 1H), 2.12 (quin, J=6.36 Hz, 1H), 1.97-1.84 (m, 2H), 1.87 (s, 3H), 1.77-1.65 (m, 2H), 1.62-1.53 (m.1H), 1.33-1.14 (m, 2H), 0.89 (d, J=6.8 Hz, 6H), 0.86 (d, J=6.8 Hz, 3H), 0.82 (d, 4H, J=6.8 Hz, 3H).

$^{13}$C NMR (100 MHz, CDCl$_3$, 298K) δ 174.9, 170.9, 156.9, 148.7, 147.9, 137.1, 136.4, 134.3, 128.6, 128.5, 127.9, 127.3, 121.7, 114.8, 112.1, 73.8, 69.9, 67.1, 66.7, 66.3, 65.6, 59.0, 56.5, 53.9, 53.2, 48.4, 42.3, 37.2, 33.2, 31.6, 31.3, 30.1, 28.1, 20.9, 20.7, 20.2, 20.1, 17.8.

EXAMPLE 24

Preparation of (2S,4S,5S,7S)-benzyl-4-acetoxy-5-(benzyloxycarbonylamino)-2,7-diisopropyl-8-[4-methoxy-3-(3-methoxypropoxy)phenyl]octanoate by the use of diphenylphosphoryl azide (DPPA)

Triethylamine (1.01 g, 10.01 mmol, 1.15 eq.) is added under nitrogen to a 250-mL three-necked flask containing a solution of the acid obtained in example 22 (5.35 g, 8.70 mmol) in toluene (50 mL). The solution is heated to 80° C. internal. At this temperature, a solution of DPPA (2.51 g, 9.14 mmol, 1.05 eq.) in toluene (10 mL) is slowly added dropwise. After addition of the first drops of DPPA solution, evolution of nitrogen is observed. After addition, it is stirred at 80° C. for 1 h.

The mixture is then brought to 50° C. and benzyl alcohol (1.88 g, 17.40 mmol, 2 eq.) is added, then it is heated under reflux for 8 hours.

The reaction mixture is cooled to room temperature and water (100 mL) is added. The phases are separated and the aqueous phase (which has pH≈7-8) is extracted with toluene (2×25 mL). The combined organic phases are dried over anhydrous sodium sulphate, filtered and concentrated in a rotary evaporator. 6.92 g of raw product are obtained, as brown oil (theoretical 6.26 g, NMR reveals the presence of benzyl alcohol).

It is purified as described in example 23.

EXAMPLE 25

Preparation of benzyl-((1S,3S)-1-(2S,4S)-4-isopropyl-5-oxotetrahydrofuran-2-yl)-3-(4-methoxy-3-(3-methoxypropoxy)benzyl)-4-methylpentyl)carbamate, Compound (IX'') in which W is Cbz

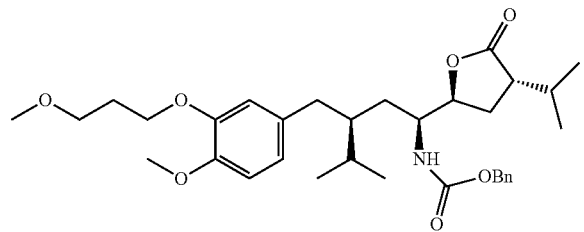 [SMILES: COCCCOc1cc(C[C@@H](C[C@H](NC(=O)OCc2ccccc2)[C@@H]2C[C@@H](C(C)C)C(=O)O2)C(C)C)ccc1OC]

A 500-mL jacketed reactor is charged with a solution of the product obtained in example 23 (17.12 g, 23.8 mmol) in ethanol (342 mL) and 10% w/w HCl in water (85.6 mL). It is heated at 70° C. for 48 hours, monitoring the cyclization reaction by HPLC. On completion of reaction, it is cooled to 0° C., stirred for 1 hour and the product obtained is filtered, washing with cold ethanol (11.31 g, yield 83.5%).

$^1$H NMR (300 MHz, CDCl$_3$, 298K) δ 7.40-7.25 (m, 5H), 6.82-6.74 (m, 2H), 6.71-6.64 (m, 1H), 5.15 & 5.10 (2×d, J=12.2 Hz, 2×1H), 4.74 (d, J=10.1, 1H), 4.36 (t, J=6.4 Hz, 1H), 4.09 (t, J=6.4 Hz, 2H), 3.86-3.78 (m, 1H), 3.82 (s, 3H), 3.55 (t, J=6.1 Hz, 2H), 2.60 (dd, J=13.8, 5.5 Hz, 1H), 2.48-2.36 (m, 2H), 2.15-1.97 (m, 5H), 1.70-1.45 (m, 3H), 1.29 (ddd, J=13.8, 9.2, 3.4 Hz, 1H), 0.95 (d, J=7.0 Hz, 3H), 0.90 (d, J=6.7 Hz, 3H), 0.82 (d, J=6.4 Hz, 3H), 0.80 (d, J=6.1 Hz, 3H).

$^{13}$C NMR (75 MHz, CDCl$_3$, 298K) δ 178.9, 157.0, 148.4, 147.7, 136.5, 133.8, 128.6, 128.2, 127.9, 121.3, 114.5, 111.9, 81.2, 69.5, 67.0, 66.1, 58.7, 56.2, 52.8, 45.8, 42.6, 37.3, 33.4, 29.7, 29.4, 28.1, 26.7, 20.4, 20.3, 18.6, 16.8.

EXAMPLE 26

Preparation of tert-butyl-((1S,3S)-1-((2S,4S)-4-isopropyl-5-oxotetrahydrofuran-2-yl)-3-(4-methoxy-3-(3-methoxypropoxy)benzyl)-4-methyl pentyl)carbamate, Compound (IX'') in which W is Boc

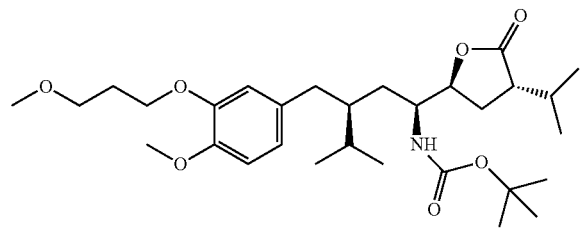 [SMILES: COCCCOc1cc(C[C@@H](C[C@H](NC(=O)OC(C)(C)C)[C@@H]2C[C@@H](C(C)C)C(=O)O2)C(C)C)ccc1OC]

Pd/C (10%, 50% moisture, 100 mg, 0.05 mmol), di-tert-butyl dicarbonate (Boc$_2$O) (2.30 g, 10.5 mmol) are added to a solution of the benzylcarbamate obtained in example 25 (5.0 g, 8.78 mmol) in methanol (50 mL); 3 cycles of vacuum/nitrogen and three cycles of vacuum/hydrogen are carried out. Hydrogenation is carried out at ambient pressure for 12 hours, then it is inertized with nitrogen and imidazole (680 mg, 10 mmol) is added, and it is stirred for two hours at room temperature. Then it is evaporated to residue, it is taken up in toluene (100 mL) and is washed with 1N HCl (20 mL), water (20 mL) and brine (20 mL), it is dried over sodium sulphate and is evaporated to residue, obtaining the desired product (4.65 g, quantitative yield) as a low-melting colourless solid.

The product thus obtained is known and the spectroscopic data ($^1$H NMR, $^{13}$C NMR, IR, [α]$_D$, MS) correspond perfectly to the data in *Organic Process Research & Development* 2010, 14, 1177-1181.

The invention claimed is:

1. A process for producing aliskiren represented by the formula (I),

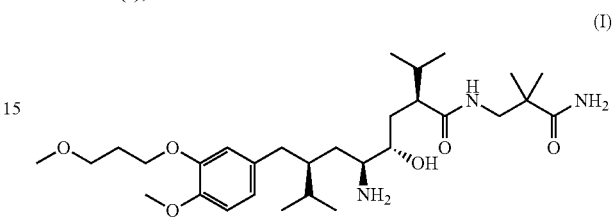

comprising the following operations:

A) converting (R)-2[4-methoxy-3-(3-methoxypropxy)benzyl]-3-methyl-butanal of formula (II)

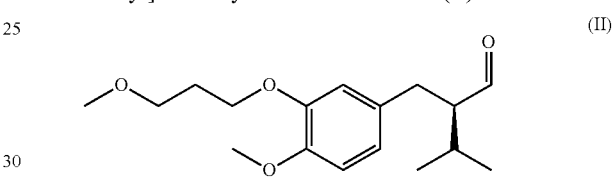

or a compound of formula (II')

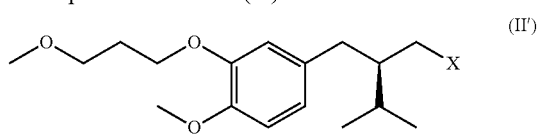

into a beta-dicarbonyl compound of formula (V)

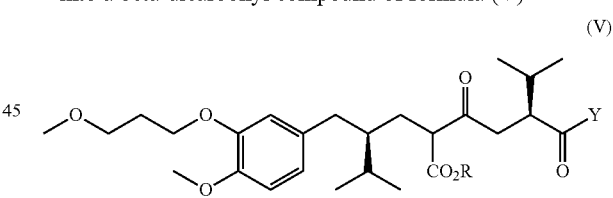

by treatment with a beta-keto ester of formula (III):

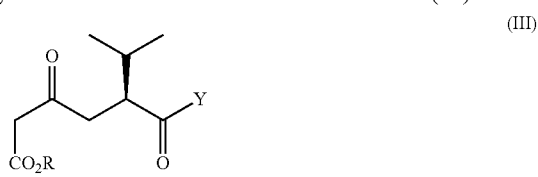

wherein R is selected from hydrogen, alkyl or alkyl-substituted, aryl or aryl-substituted; and Y is selected from: an —OR$^1$ group, in which R$^1$ has the same meanings above defined for R; radical (S)-4-benzyloxazolidin-2-on-3-yl; or radical 2-carbamoyl-2-methylpropylamino; and X is a leaving group;

B) transforming the compound (V) into the intermediate of formula (VII):

(VII)

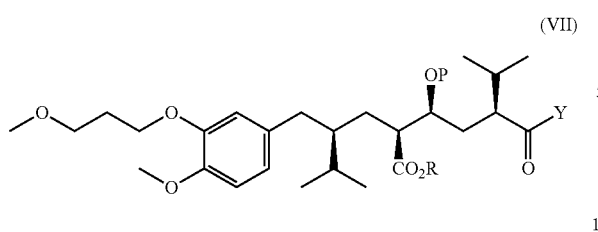

wherein P is selected from radicals hydrogen; acyl, $R^2C(O)$—, in which $R^2$ has the same meanings above defined for R; silyl, $R^3{}_3Si$—, in which $R^3$ has the same meanings above defined for R; and carbamoyl, $R^4{}_2NC(O)$—, in which $R^4$ has the same meanings above defined for R;

C) transforming the intermediate (VII) into a cyclic carbamate or an amino-lactone, respectively represented by the formula (VIII) or (IX"), wherein W is hydrogen or —$C(O)OR^5$ and in which $R^5$ has the same meanings above defined for R:

(IX")

(VIII)

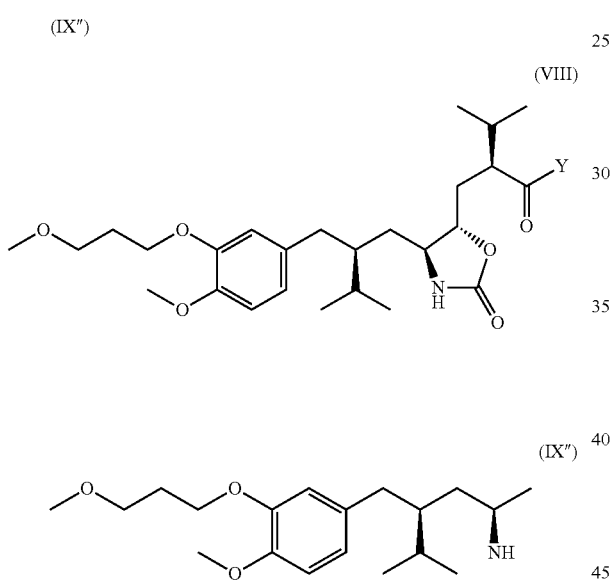

(IX")

D) transforming the cyclic carbamate (VIII) or the amino-lactone (IX") into aliskiren of formula (I) by reaction with 3-amino-2,2-dimethylpropanamide, of formula

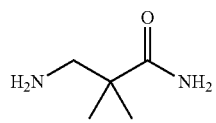

and subsequent hydrolysis of the cyclic carbamate or deprotection of the amino group.

2. The process according to claim 1, wherein operation A is carried out according to a reaction pathway A.i) that consists of the following operations:

A.i.1): reaction of compound (R)-2-[4-methoxy-3-(3-methoxypropoxy)benzyl]-3-methyl-butanal of formula (II)

(II)

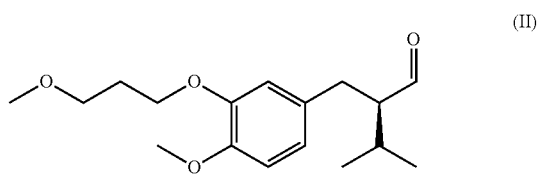 [SMILES: COCCCOc1cc(C[C@@H](C=O)C(C)C)ccc1OC]

with beta-keto ester of formula (III), (III)

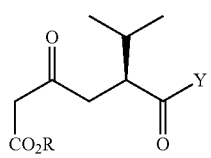

to form the compound of formula (IV):

(IV)

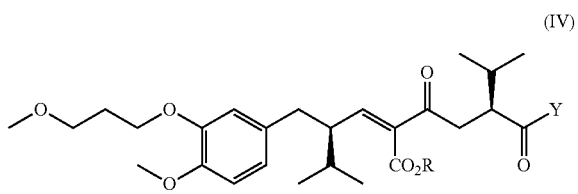

wherein, in the formula of compound (IV), symbol ╱╱╱╱ indicates that the double bond —C═C— may have configuration E or Z;

A.i.2): hydrogenation, in an inert solvent with hydrogen at a pressure comprised between 1 and 10 bar and with metal catalysts selected from the group consisting of nickel Raney or nickel, palladium or platinum on inert support, of the double bond —C═C— of compound (IV) obtained in reaction A.i.1) to form compound (V).

3. The process according to claim 1, wherein operation A is carried out according to a reaction pathway A.ii) that consists of reacting the derivative of compound (R)-2-[4-methoxy-3-(3-methoxypropoxy)benzyl]-3-methyl-butyl of formula (II'), (II')

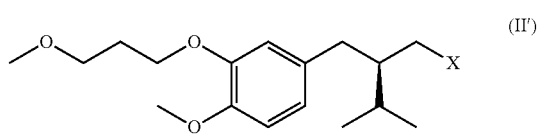

wherein X is as leaving group, with beta-keto ester of formula (III), (III)

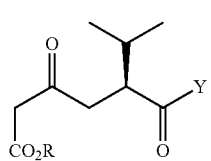

to form product (V):

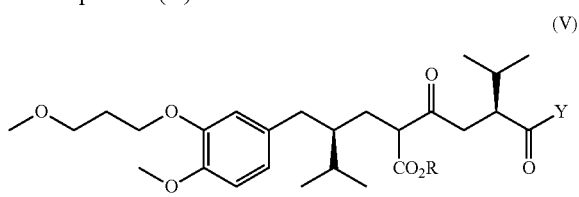
(V)

wherein said reaction takes place in a protic or non-protic polar solvent in the presence of an inorganic base at a temperature comprised between about 20° C. and the solvent reflux temperature.

4. The process according to claim 1, wherein operation B is carried out according to a reaction pathway B.i) that consists of the operations:

B.i.1): forming, starting from compound (V), the enol ether of formula (VI):

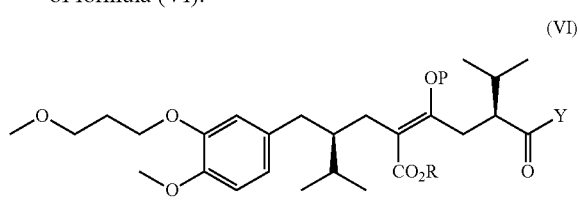
(VI)

by treating compound (V) with an acylating agent or a silylating agent and an organic or inorganic base, optionally in an inert solvent such as dichloromethane or toluene;

B.i.2): hydrogenating compound (VI) to form compound (VII) by the use of a catalyst based on a transition metal selected from the group consisting of ruthenium, rhodium, iridium, nickel, palladium, platinum or salts thereof optionally as a mixture, optionally supported on an inert matrix, or by the use of a transition metal in the form of a complex soluble in the reaction medium optionally coordinated with a chiral mono- or bidentate phosphine in the form of racemic mixture, in enantiomerically enriched form or in the form of a single enantiomer, or with an achiral mono- or bidentate phosphine.

5. The process according to claim 4, wherein the hydrogenation operation is carried out with a homogeneous catalyst of iridium or rhodium selected from the group consisting of [IrCl(1,4-cyclooctadiene)]2, [RhCl(1,4-cyclooctadiene)]2, and [Rh(norbornadiene)2]BF4 coordinated with a bidentate phosphine.

6. The process according to claim 1, wherein operation B is carried out according to a reaction pathway B.ii) that consists in the direct bio-transformation of compound (V) into compound (VII), through the use of enzymes or micro-organisms with cheto-reductase activity, in the presence of a co-factor such as NAD and optionally in the presence of a system capable of regenerating the co-factor.

7. The process according to claim 1, wherein operation B is carried out according to a reaction pathway B.iii) that consists of the direct asymmetrical hydrogenation of compound (V) to yield compound (VII), by the use of homogeneous catalysts based on Ru(II) and chiral bidentate phosphines.

8. The process according to claim 1, wherein in operation C compound (VII)

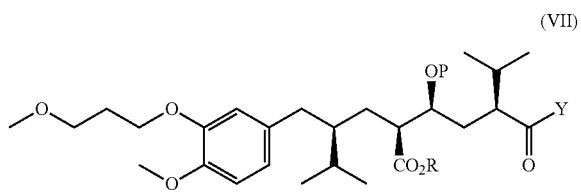
(VII)

is transformed into the cyclic carbamate of formula (VIII)

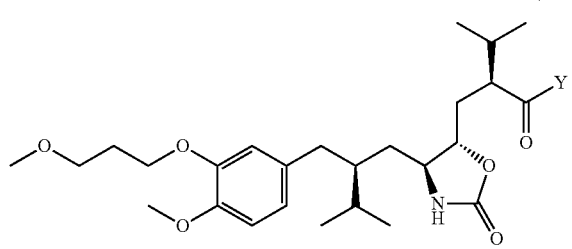
(VIII)

according to a reaction pathway C.i) that consists of the following reactions:

C.i.1): transforming the intermediate (VII) into an intermediate (VII')

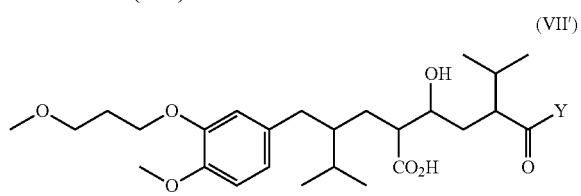
(VII')

through one or more hydrolysis reactions or deprotection of the ester and/or alcohol group;

C.i.2): transformation reaction of the intermediate (VII') into an isocyanate (VII'') (optionally isolated); and C.i.3): intramolecular reaction between the alcohol group and the isocyanate group of compound (VII'')

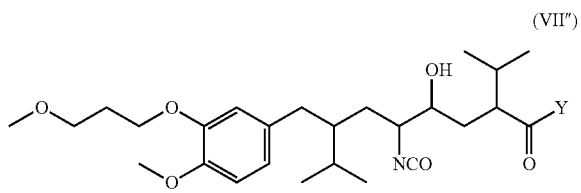
(VII'')

to yield cyclic carbamate (VIII):

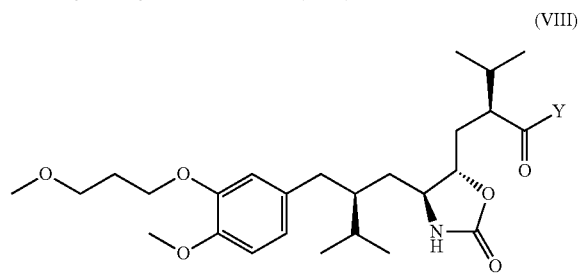
(VIII)

9. The process according to claim 1, wherein in operation C compound (VII)

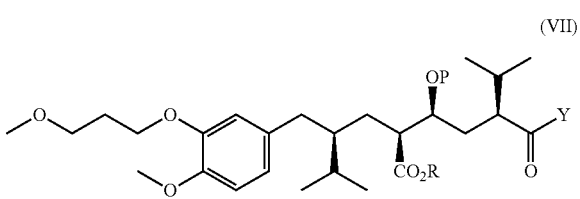

is transformed into the amino-lactone of formula (IX″)

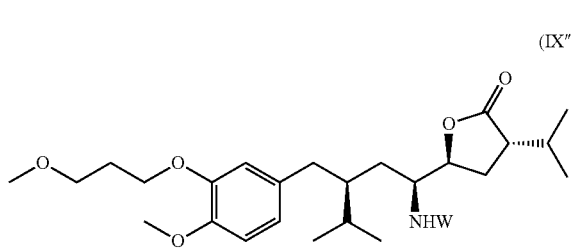

according to a reaction pathway C.ii) that consists of the following reactions:
C.ii.1): if P is not H, removal of the protection of the alcoholic function;
C.ii.2): lactonization of the alcohol of formula (VII‴)

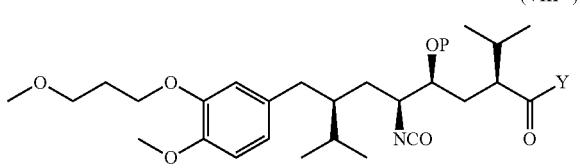

catalysed by organic or inorganic acids or bases or induced by a dehydrating agent:
C.ii.3): removal of group R, if different from hydrogen;
C.ii.4): transformation of the lactone of formula (IX)

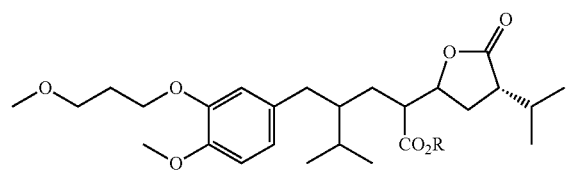

wherein R=H into an isocyanate of formula (IX′)

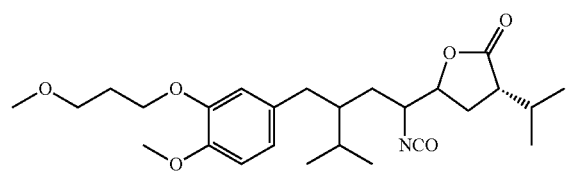

through a Curtius reaction and subsequent treatment of (IX′) with an alcohol ROH in the presence of an organic base to give the protected amino-lactone (IX″), or direct transformation of (IX) into (IX″) by Curtius reaction in the presence of an alcohol ROH.

10. The process according to claim 1, wherein in operation C compound (VII) is transformed into the amino-lactone of formula (IX″) according to a reaction pathway C.iii) that consists in the following reactions:
C.iii.1) removal, if present, of the protecting group R of the ester of intermediate (VII)

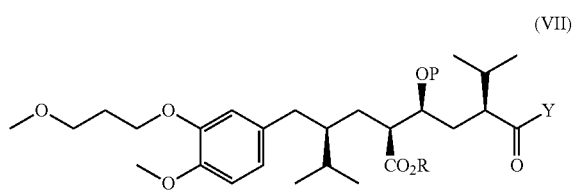

to yield the corresponding acid;
C.iii.2) transformation of the thus obtained acid into the isocyanate (VII‴),

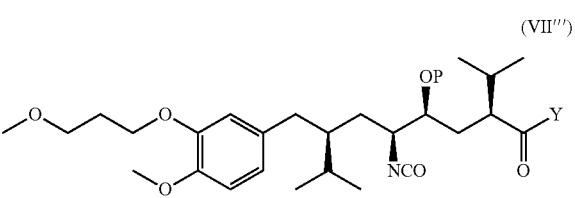

optionally isolated, through a Curtius reaction;
C.iii.3) reaction of isocyanate (VII‴) with an alcohol to yield a carbamate (VII⁗)

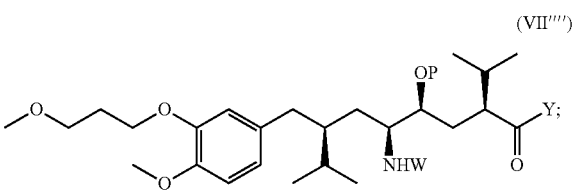

C.iii.4) hydrolysis (simultaneous or in sequence) of groups P and Y and cyclization of the resulting hydroxyacid to yield lactone (IX″)

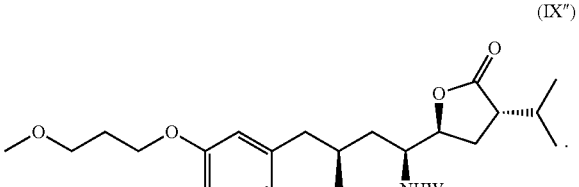

11. The process according to claim 2, wherein the reaction of operation A.i.1) takes place in a non-protic polar or apolar solvent in the presence of a catalyst selected from the group consisting of piperidine, morpholine, and pyridine, optionally along with an equal stoichiometric amount of an organic acid and operating at a temperature between about 20 and 50° C.

12. The process according to claim 2, wherein the reaction of operation A.i.1) takes place using a stoichiometric amount of titanium tetrachloride and pyridine in an inert solvent at a temperature between −20 and 20° C.

13. The process according to claim 4, wherein the hydrogenation reaction of operation B.i.2) is carried out in a protic or non-protic solvent at a pressure between 5 and 30 bar and at a temperature between 40 and 80° C.

14. The process according to claim 1, in which P is selected from the group consisting of acetyl, trimethylsilyl, tert-butyldimethylsilyl, tert-butyldiphenylsilyl, and dimethylcarbamoyl.

15. The process according to claim 5, wherein the hydrogenation operation is carried out using (S)-(+)-4,12-Bis(diphenylphosphino)-[2.2]-paracyclophane)Rh(1-4-cyclooctadiene)]$BF_4$ as the catalyst.

16. The process according to claim 13, wherein, when in the enol compound (VI) R is hydrogen, said compound is used in the form of a salt thereof with a tertiary alkyl amine.

\* \* \* \* \*